(12) United States Patent
Hori et al.

(10) Patent No.: US 9,044,605 B2
(45) Date of Patent: Jun. 2, 2015

(54) BEAM MONITOR SYSTEM AND PARTICLE BEAM IRRADIATION SYSTEM

(71) Applicant: Hitachi, Ltd., Tokyo (JP)

(72) Inventors: Yoshihito Hori, Tokyo (JP); Kunio Moriyama, Tokyo (JP); Tomohisa Iwamoto, Tokyo (JP); Masahiro Tadokoro, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/446,658

(22) Filed: Jul. 30, 2014

(65) Prior Publication Data

US 2015/0041673 A1    Feb. 12, 2015

(30) Foreign Application Priority Data

Aug. 7, 2013  (JP) .................................. 2013-164438

(51) Int. Cl.
*A61N 5/10*    (2006.01)

(52) U.S. Cl.
CPC ............ *A61N 5/1065* (2013.01); *A61N 5/1077* (2013.01); *A61N 2005/1074* (2013.01)

(58) Field of Classification Search
USPC ............................................. 250/397, 492.3
See application file for complete search history.

(56) References Cited

U.S. PATENT DOCUMENTS

| | | | |
|---|---|---|---|
| 8,674,319 | B2 | 3/2014 | Iwamoto et al. |
| 2012/0305796 | A1 | 12/2012 | Iseki et al. |
| 2013/0231517 | A1* | 9/2013 | Iwamoto et al. .................. 600/1 |

FOREIGN PATENT DOCUMENTS

GB    2499896 A    9/2013

OTHER PUBLICATIONS

Chu et al., "Instrumentation for treatment of cancer using proton and light-ion beams", Review of Scientific Instruments, Aug. 1993, vol. 64, No. 8, pp. 2074-2093.
European Search Report received in corresponding European Application No. 14179645 dated Dec. 23, 2014.
T. Nakamura et al., "A half-millimetre spacial resolution fibre-coded linear position-sensitive scintillator detector with wavelength-shifting fibre read-out for neutron detection", Nuclear Instruments & Methods in Physics Research, Section A: Accelerators, Spectrometers, Detectors, and Associated Equipment, Elsevier BV, North-Holland, vol. 606, No. 3, Jul. 21, 2009, pp. 675-680.

* cited by examiner

*Primary Examiner* — Kiet T Nguyen
(74) *Attorney, Agent, or Firm* — Mattingly & Malur, P.C.

(57) ABSTRACT

A charge collection electrode is formed of a plurality of groups each of which is made up of a plurality of adjoining wire electrodes. Further, all the wire electrodes are connected to channels of a signal processing device by the same number of lines as the wire electrodes belonging to one group so that each detection signal outputted from one wire electrode selected from each group is inputted through the same line and so that no two adjoining channels are physically continuous in regard to a certain set of consecutive measurement channels. The signal processing device determines group information indicating to which group the wire electrodes that sent the inputted detection signals belong and outputs a processing signal including the group information to a beam monitor controller. The beam monitor controller determines the position and the beam width of the charged particle beam that passed through the wire electrodes.

8 Claims, 17 Drawing Sheets

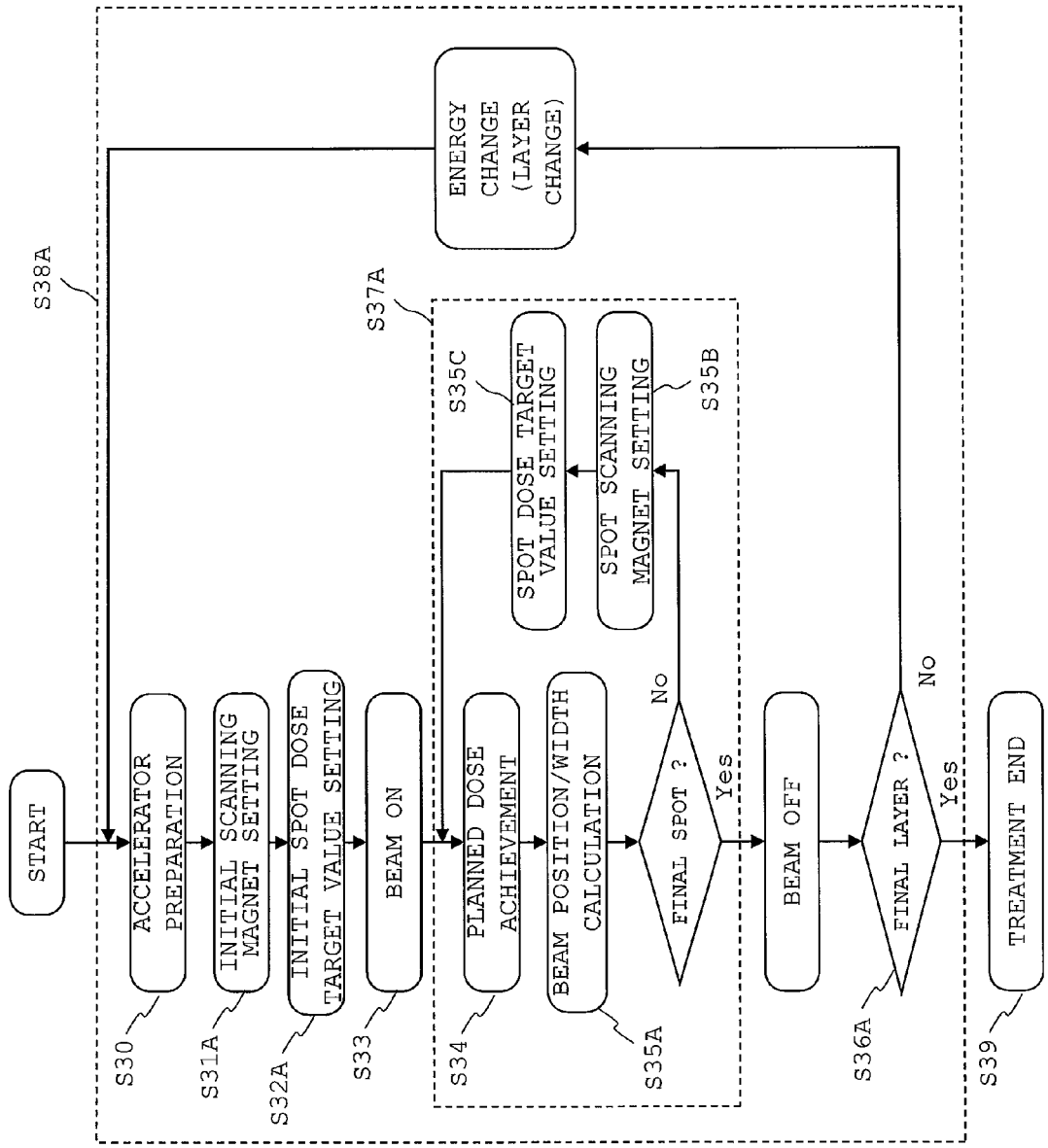

BEAM MONITOR SYSTEM AND PARTICLE BEAM IRRADIATION SYSTEM

BACKGROUND OF THE INVENTION

The present invention relates to a beam monitor system for monitoring the beam position in a charged particle beam (particle beam) irradiation system. In particular, the present invention relates to a beam monitor system for a particle beam irradiation system that can be suitably employed for a particle therapy system for treating affected parts (infected parts) by irradiating the affected parts with a particle beam of protons, carbon ions, etc.

There is a well-known method of treating cancer patients, etc. by irradiating an affected part in the patient's body with a charged particle beam (particle beam, ion beam) such as a proton beam or a carbon ion beam. The particle beam irradiation system used for the treatment comprises a charged particle beam generator. The ion beam accelerated by the charged particle beam generator reaches an irradiation device (irradiation nozzle) installed in a rotating gantry via a first beam transport line and a second beam transport line which is arranged in the rotating gantry. The ion beam is emitted from the irradiation device and applied to the affected part in the patient.

Various known irradiation methods can be employed by the irradiation device (see Review of Scientific Instruments, Volume 64, Number 8 (August 1993), Pages 2074-2093, for example). Such irradiation methods include the double scattering method in which the beam is broadened by use of a scatterer and then cut out in conformity with the shape of the affected part (see page 2081 and FIG. 35 of the above literature), the wobbler method (see page 2084 and FIG. 41 of the above literature), and the scanning method in which a thin beam is scanned within the target area (see pages 2092 and 2093 of the above literature).

SUMMARY OF THE INVENTION

Among the aforementioned beam irradiation methods, the scanning method is attracting great attention due to its advantage that influence on normal cells is slight and no in-nozzle instrument is necessary. The scanning method is characterized in that the beam irradiation is performed in conformity with the shape of the irradiation target (affected part) while successively changing the irradiation position of the charged particle beam (called a "spot") by interrupting the emission (extraction) of the charged particle beam according to the dose (amount of irradiation) on the irradiation target, changing the irradiation position (spot) by controlling the energy and the scanning magnet, and restarting the extraction of the charged particle beam after completing the change of the irradiation position.

In such a charged particle irradiation system, a beam position monitor (hereinafter referred to as a "spot position monitor") is arranged at a position downstream of the scanning magnet and immediately before the patient (irradiation target) in order to achieve the irradiation in conformity with the shape of the affected part.

The spot position monitor is made up of detectors each of which is called a "multi-wire" (hereinafter referred to as a "channel"). For each channel, electric charges caused by the passage of the beam are accumulated in a capacitor and induced voltage is read out. Since the signal detected by each channel is weak, an amplifier is arranged downstream of each channel. The signal detected by each channel (detection signal) is sent to a signal processing device via the amplifier. The signal processing device is capable of detecting the position and the width of the beam by use of the detection signals received from all the multi-wires.

To improve the beam position/width detection accuracy of the spot position monitor, it is possible to increase the number of channels. The spot position monitor needs a plurality of signal amplifiers and signal processing devices corresponding to the number of channels. For the detection of the beam position and the beam width, the signal amplification and the signal processing are executed for all the channels. Thus, with the increase in the number of channels, the monitor system is necessitated to be large-sized and complicated and the cost rises accordingly.

It is therefore the primary object of the present invention to provide a beam monitor system capable of precisely performing the position determination and making the judgment on whether the irradiation is appropriate or not with higher accuracy in the spot irradiation according to the scanning method, and to provide a particle beam irradiation system comprising such a beam monitor system.

To achieve the above object, configurations described below can be employed. While the present invention contains a plurality of means for achieving the above object, the following configuration can be employed, for example: An aspect of the present invention provides a beam monitor system comprising a collection electrode for detecting a charged particle beam passing therethrough, a signal processing device, and a beam monitor controller. The collection electrode includes a plurality of groups each of which is made up of a plurality of adjoining wire electrodes and divided into segments each including a plurality of adjoining wire electrodes. Each wire electrode in a segment in a group is connected to the signal processing device by using the same line as a wire electrode in a segment in each of the other groups. The wire electrodes in each segment in each of the other groups are connected to the signal processing device by employing permutation connection varying from group to group so that no two adjoining channels are physically continuous. The signal processing device rearranges detection signals outputted from the wire electrodes based on information related to a planned beam irradiation target position and information on the permutation connection and outputs the result of the rearrangement as a processing signal. The beam monitor controller calculates the beam position and the beam width of the charged particle beam that passed through the wire electrodes based on the processing signal outputted from the signal processing device.

According to the present invention, a beam monitor system capable of precisely detecting not only beam irradiation at correct positions but also beam irradiation at erroneous positions can be realized. The position determination can be performed precisely and the judgment on whether the irradiation is appropriate or not can be made with higher accuracy in the spot irradiation according to the scanning method.

BRIEF DESCRIPTION OF THE DRAWINGS

FIG. 17 is a flow chart of charged particle beam irradiation control according to the raster scan method.

DESCRIPTION OF THE PREFERRED EMBODIMENTS

Figure 1:
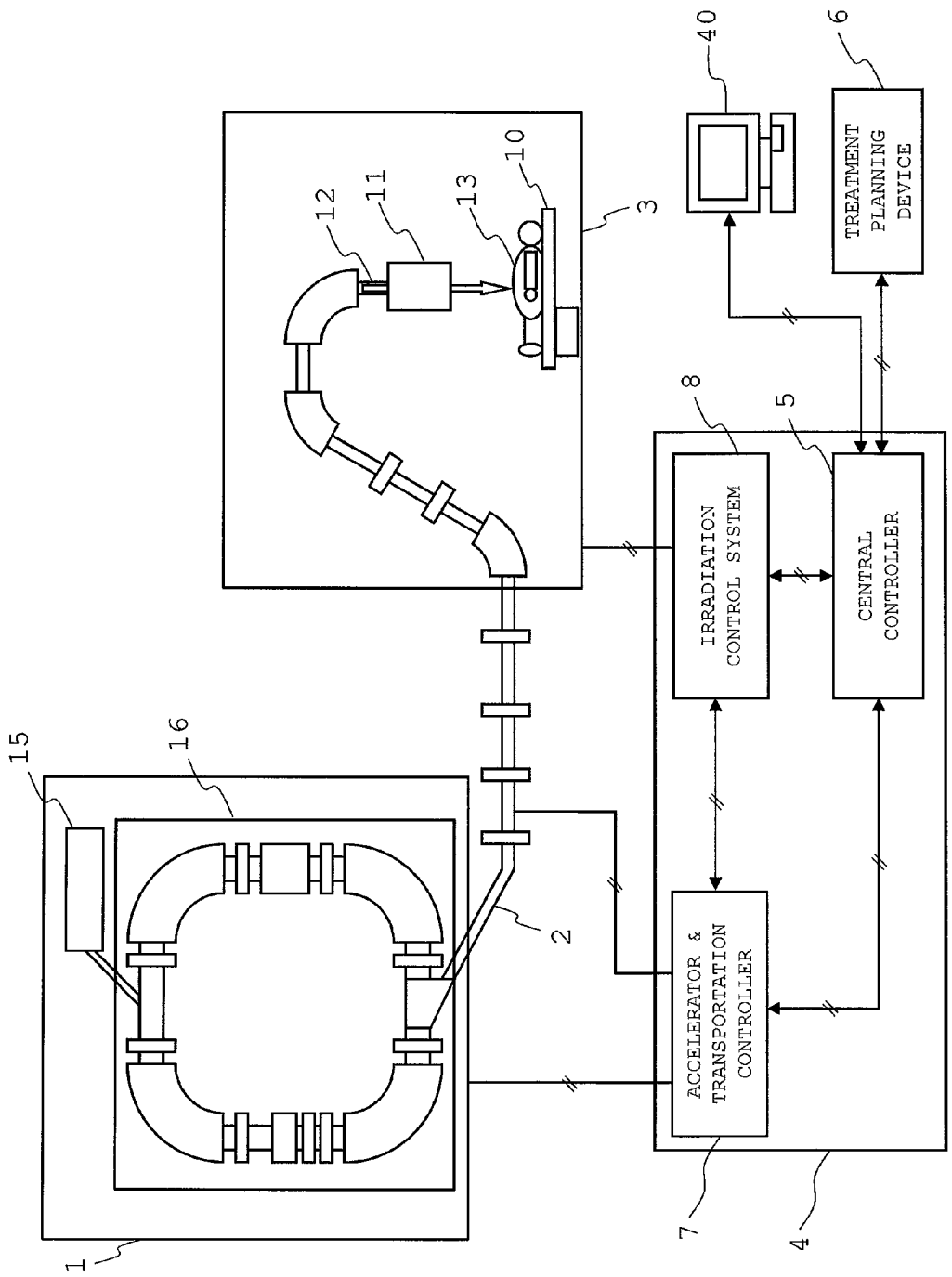
FIG. 1 is a schematic diagram showing the overall configuration of a particle beam irradiation system according to a first embodiment of the present invention.

Referring to the drawings, a description will be given in detail of preferred embodiments of the beam monitor system and the particle beam irradiation system in accordance with the present invention.

First Embodiment

A first embodiment of the beam monitor system and the particle beam irradiation system in accordance with the present invention will be described below referring to FIGS. 1-14.

In the present invention, the particle beam irradiation system means a system for applying a charged particle beam 12 (proton beam, heavy ion beam, etc.) to a affected part in a patient fixed on a couch (bed apparatus) 10 in a treatment room.

First, the configuration of the particle beam irradiation system according to the present invention will be explained by referring to FIGS. 1-4.

Figure 2:
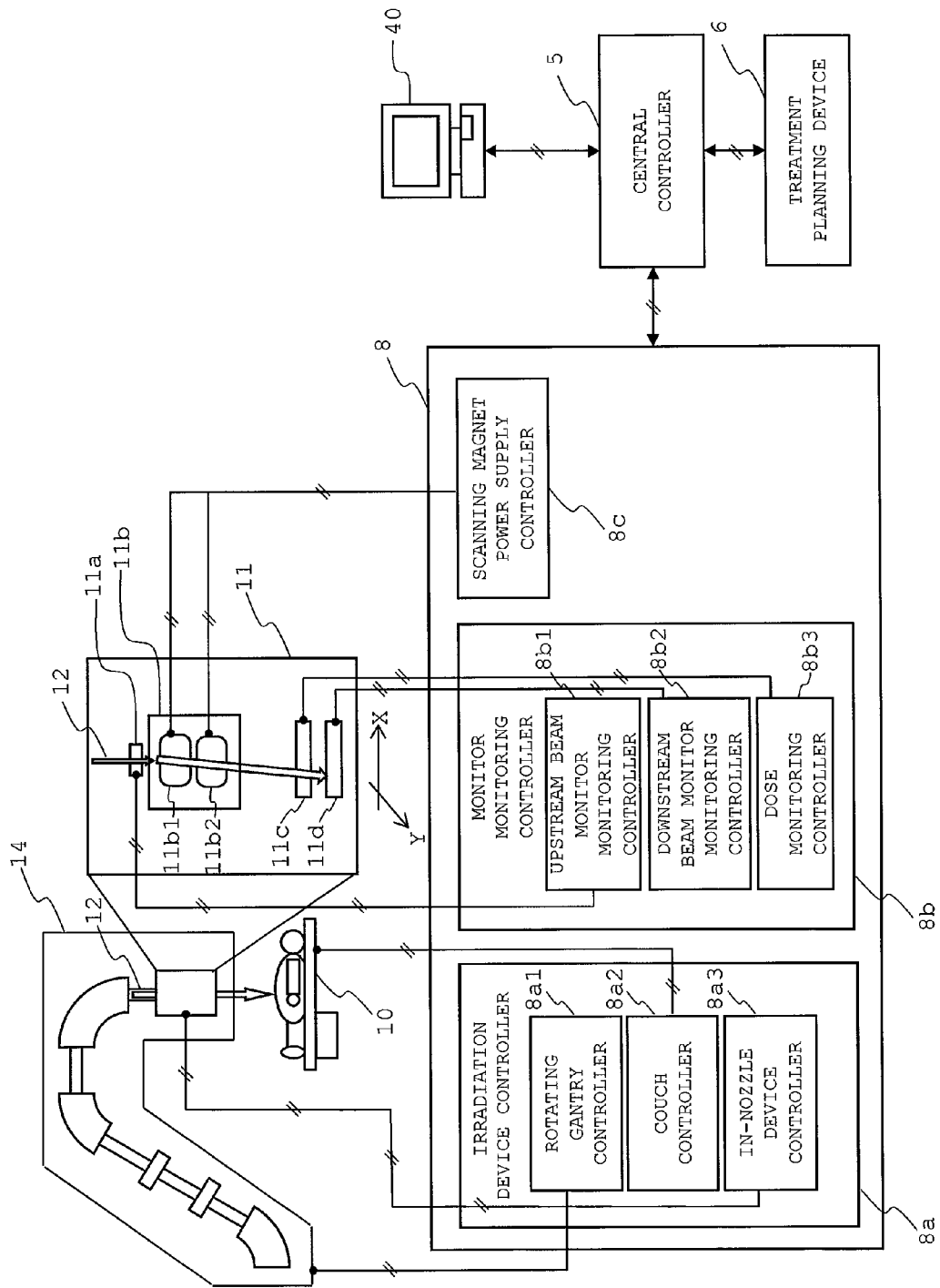
FIG. 2 is a schematic diagram showing the outline of a scanning irradiation system and an irradiation control system constituting the particle beam irradiation system according to the first embodiment of the present invention.
Figure 3:
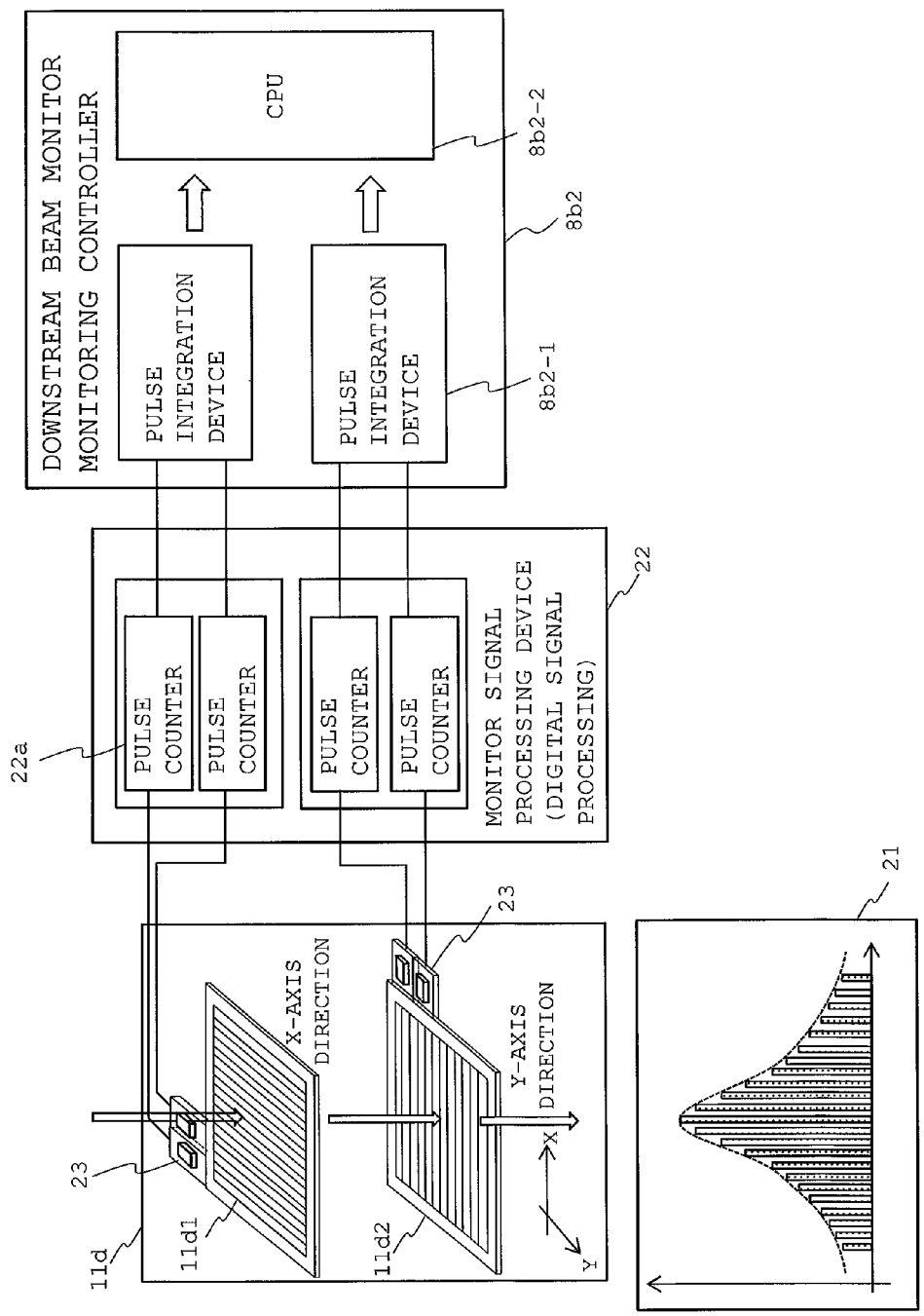
FIG. 3 is a schematic diagram showing the outline of a beam monitor system in the particle beam irradiation system according to the first embodiment of the present invention.
Figure 4:
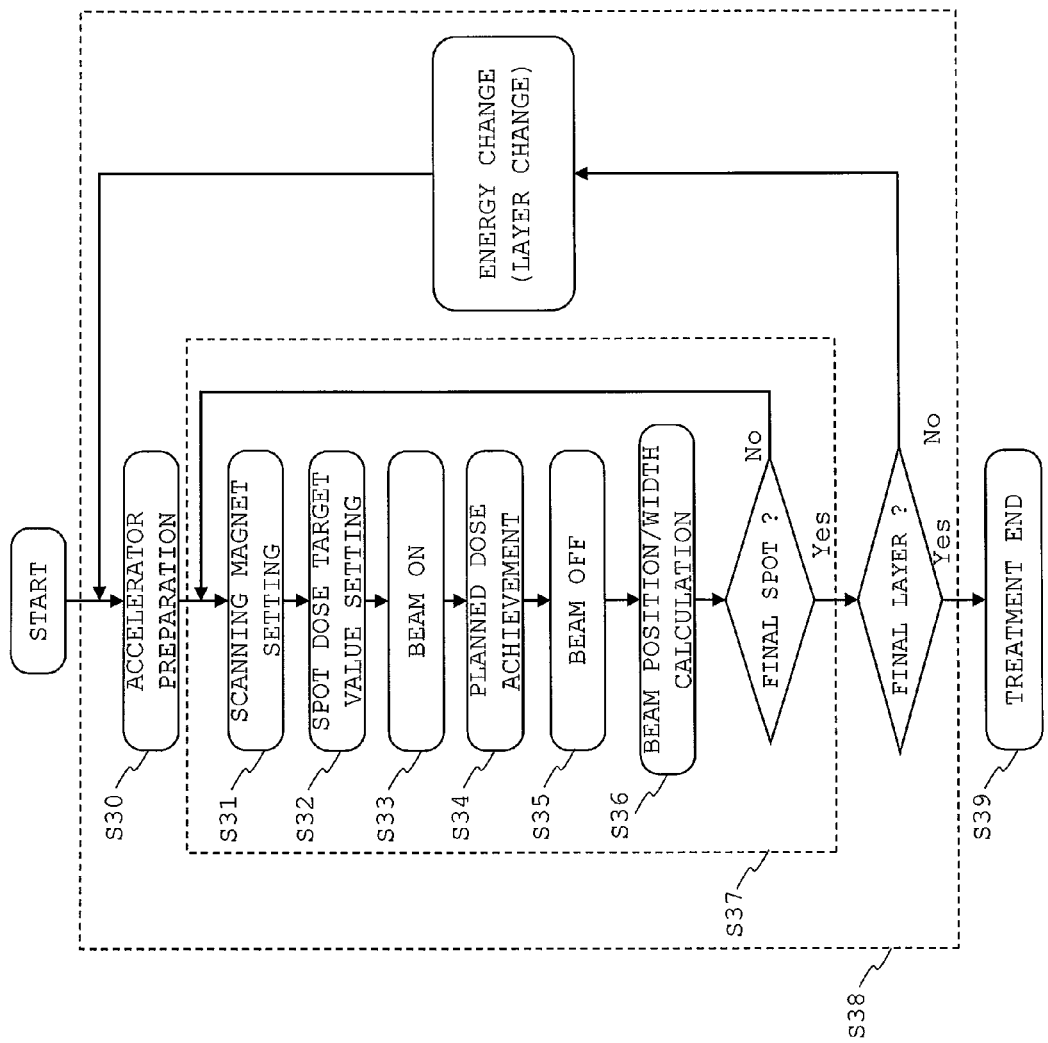
FIG. 4 is a flow chart showing the flow of charged particle beam irradiation control according to the scanning irradiation method.

FIG. 1 is a schematic diagram showing the overall configuration of a particle beam irradiation system according to the first embodiment of the present invention. FIG. 2 is a schematic diagram showing the outline of a scanning irradiation system and an irradiation control system constituting the particle beam irradiation system according to the first embodiment of the present invention. FIG. 3 is a schematic diagram showing the outline of a beam monitor system in the particle beam irradiation system according to the first embodiment of the present invention. FIG. 4 is a flow chart showing the flow of charged particle beam irradiation control according to the scanning irradiation method.

The particle beam irradiation system in this embodiment mainly comprises a charged particle beam generator 1, a beam transport line 2, a scanning irradiation device 3, and a control system 4.

The charged particle beam generator 1 includes an ion source (not shown), a linear accelerator (hereinafter referred to as a "LINAC") 15, and a circular accelerator (synchrotron) 16. While this embodiment will be explained by taking a synchrotron as an example of the circular accelerator 16, other types of accelerators such as a cyclotron may also be employed as the circular accelerator 16. The ion source is connected upstream of the LINAC 15. The circular accelerator 16 is connected downstream of the LINAC 15.

The beam transport line 2 is connected downstream of the charged particle beam generator 1 so as to connect the charged particle beam generator 1 to the scanning irradiation device 3.

The scanning irradiation device 3 is a device for applying the charged particle beam 12 to the affected part in the patient. As shown in FIG. 2, the scanning irradiation device 3 mainly includes the couch 10 on which the patient 13 is set, an irradiation nozzle (nozzle device) 11, and a rotating gantry 14.

The couch 10 is arranged in the treatment room. The patient 13 is set on the couch 10 and the positioning of the affected part is done by use of the couch 10.

As shown in FIG. 2, the irradiation nozzle 11 includes an upstream beam monitor 11a, a scanning magnet 11b, a dose monitor 11c and a downstream beam monitor 11d which are arranged along the beam path from the upstream side in the propagation direction of the charged particle beam 12. The irradiation nozzle 11 forms the irradiation field of the scanning beam.

The upstream beam monitor 11a measures the passage position and the beam width (beam diameter) of the charged particle beam 12 entering the irradiation nozzle 11.

The scanning magnet 11b includes a first scanning magnet 11b1 for deflecting/scanning the passing charged particle beam in a first direction (e.g., X-axis direction) and a second scanning magnet 11b2 for deflecting/scanning the charged particle beam in a second direction (e.g., Y-axis direction) orthogonal to the first direction. Here, the X-axis direction means a direction in a plane orthogonal to the propagation direction of the charged particle beam entering the irradiation nozzle 11. The Y-axis direction means a direction in the plane and orthogonal to the X-axis.

The dose monitor 11c measures the dose of the passing charged particle beam. In other words, the dose monitor 11c is a device (monitor) for monitoring the dose of the charged particle beam irradiating the patient.

The downstream beam monitor $11d$ is arranged downstream of the scanning magnet $11b$ and measures the position and the beam width of the passing charged particle beam. In other words, the downstream beam monitor $11d$ is a monitor for measuring the position and the beam width of the charged particle beam scanned by the scanning magnet $11b$.

The rotating gantry 14 is configured to be rotatable around the isocenter (not shown). The rotating gantry 14 sets the irradiation angle of the beam. The rotation of the rotating gantry 14 enables to change the irradiation angle of the charged particle beam 12 irradiating the patient 13.

As shown in FIG. 1, the control system 4 mainly includes a central controller 5, an accelerator/transportation controller 7, and an irradiation control system 8.

The central controller 5 is connected to a treatment planning device 6, the accelerator/transportation controller 7, the irradiation control system 8, and an operation terminal 40. The central controller 5 has functions of calculating setup values of operation parameters for operating the accelerators and operation parameters for forming the irradiation field and setup values of the planned beam position, beam width and dose based on setting data supplied from the treatment planning device 6. These operation parameters and monitor setup values are outputted from the central controller 5 to the accelerator/transportation controller 7 and the irradiation control system 8.

The accelerator/transportation controller 7 is connected to the charged particle beam generator 1 and the beam transport line 2. The accelerator/transportation controller 7 has a function of controlling devices constituting the charged particle beam generator 1 and the beam transport line 2.

The irradiation control system 8 is connected to the scanning irradiation device 3. The irradiation control system 8 controls devices constituting the scanning irradiation device 3.

The operation terminal 40 includes a display screen and an input device for allowing the operator (medical staff such as a doctor or an operator) to input data and command signals.

The irradiation control system 8 will be explained below referring to FIG. 2.

The irradiation control system 8 includes an irradiation device controller $8a$, a monitor monitoring controller $8b$, and a scanning magnet power supply controller $8c$.

The irradiation device controller $8a$ includes a rotating gantry controller $8a1$ for controlling devices constituting the rotating gantry 14, a couch controller $8a2$ for moving the couch 10 and performing the positioning control of the couch 10, and an in-nozzle device controller $8a3$ for controlling devices arranged in the irradiation nozzle 11. The rotating gantry controller $8a1$ controls the irradiation angle of the charged particle beam irradiating the patient 13 by controlling the rotation angle of the rotating gantry 14.

The monitor monitoring controller $8b$ mainly includes an upstream beam monitor monitoring controller $8b1$ for performing monitoring control on the upstream beam monitor $11a$, a downstream beam monitor monitoring controller $8b2$ for performing monitoring control on the downstream beam monitor $11d$, and a dose monitoring controller $8b3$ for performing monitoring control on the dose monitor $11c$.

The upstream beam monitor monitoring controller $8b1$ has a function of measuring the beam position and the beam width of the charged particle beam entering the upstream beam monitor $11a$ and a function of judging whether there is an abnormality in the charged particle beam or not (error detection processing).

The downstream beam monitor monitoring controller $8b2$ has a function of measuring the beam position and the beam width of the charged particle beam scanned by the scanning magnet $11b$ and entering the downstream beam monitor $11d$. Specifically, the downstream beam monitor monitoring controller $8b2$ has a function of judging whether there is an abnormality in the beam position and the beam width of the scanned charged particle beam (error detection processing). An example of concrete mechanisms of the upstream beam monitor monitoring controller $8b1$ and the downstream beam monitor monitoring controller $8b2$ will be described below.

The upstream beam monitor monitoring controller $8b1$ calculates the passage position and the beam width of the charged particle beam by performing a calculation process on measurement data received from the upstream beam monitor $11a$. When the calculated beam position is outside a preset range or the calculated beam width is outside a preset range, the upstream beam monitor monitoring controller $8b1$ judges that there is an abnormality in the beam and outputs an abnormality signal to the central controller 5.

The downstream beam monitor monitoring controller $8b2$ calculates the passage position and the beam width of the charged particle beam by performing a calculation process on measurement data received from the downstream beam monitor $11d$. When the calculated beam position is outside a preset range or the calculated beam width is outside a preset range, the downstream beam monitor monitoring controller $8b2$ judges that there is an abnormality in the beam and outputs an abnormality signal to the central controller 5.

When the abnormality signal is inputted from the upstream beam monitor monitoring controller $8b1$ or the downstream beam monitor monitoring controller $8b2$, the central controller 5 outputs a beam stop command signal to the accelerator/transportation controller 7 and thereby stops the charged particle beam extracted from the charged particle beam generator 1.

Incidentally, while the central controller 5 in this embodiment performs the control so as to stop the charged particle beam extracted from the charged particle beam generator 1, the central controller 5 may also perform the control so as to stop the charged particle beam entering the irradiation nozzle 11 by controlling the beam transport line 2.

Here, the "beam position" of the charged particle beam means the barycentric position of the charged particle beam passing through the beam monitor (the upstream beam monitor $11a$ or the downstream beam monitor $11d$), for example.

The "beam width" of the charged particle beam represents the region of the passage of the charged particle beam through the beam monitor (the upstream beam monitor $11a$ or the downstream beam monitor $11d$). The beam width can be determined by calculating the area of the region of detection of the charged particle beam by a beam monitor (the upstream beam monitor $11a$ or the downstream beam monitor $11d$) arranged on a plane orthogonal to the beam propagation direction, or by calculating the area and the width of the charged particle beam detection region by such a beam monitor, for example.

The scanning magnet power supply controller $8c$ controls a power supply unit (not shown) of the scanning magnet $11b$ and thereby controls the excitation current for the scanning magnet $11b$ and changes the irradiation position of the charged particle beam (position of irradiation of the patient 13 with the charged particle beam).

Next, the flow from the start to the end of the treatment for the patient will be explained below by referring to FIG. 4.

In this embodiment, the following explanation will be given by taking the spot scanning irradiation as an example of the irradiation method. In the spot scanning irradiation, the affected part in the patient 13 is divided into a plurality of layers successively arranged in the beam propagation direction (depth direction extending from the body surface of the patient 13) and the beam irradiation is performed on each layer while dividing the layer into a plurality of small regions (spots).

The treatment planning device 6 has stored previously acquired treatment plan information for the patient. The treatment plan information includes irradiation data (beam energy information, irradiation position information, a target dose value of the charged particle beam for each irradiation position, etc.) and permissible value data (permissible beam position information and permissible beam width information regarding the upstream beam monitor 11a, permissible beam position information and permissible beam width information regarding the downstream beam monitor 11d in regard to each irradiation position, etc.).

Incidentally, while the irradiation data and the permissible value data are determined by the treatment planning device 6 in this embodiment, this embodiment may also be configured so that the irradiation data are determined by the treatment planning device 6 and the permissible value data are determined by the central controller 5. In this case, the treatment planning device 6 sends data necessary for the determination of the permissible value data to the central controller 5, and the central controller 5 calculates the permissible value data based on the data received from the treatment planning device 6. The target dose value included in the irradiation data is determined for each spot position in each layer.

After the patient 13 has been fixed on the couch (bed) 10, the doctor inputs a preparation start signal through the input device of the operation terminal 40.

The central controller 5 receiving the preparation start signal acquires the treatment plan information on the patient from the treatment planning device 6 and outputs bed position information to the couch controller 8a2. Based on the bed position information, the couch controller 8a2 moves and position of the couch 10 so as to place the patient 13 at a prescribed position on an extension line of the beam axis. The central controller 5 also outputs gantry angle information to the rotating gantry controller 8a1. Based on the gantry angle information, the rotating gantry controller 8a1 rotates the rotating gantry 14 and sets the gantry at a prescribed angle. The central controller 5 also sends the target dose value of the charged particle beam for each irradiation position and the permissible value data to the monitor monitoring controller 8b. The central controller 5 determines excitation current parameters by calculating excitation current values for the scanning magnet 11b (values of the excitation currents for exciting the scanning magnet 11b) based on the beam energy information and the irradiation position information included in the irradiation data, and sends the excitation current parameters to the scanning magnet power supply controller 8c. Further, based on the treatment plan information, the central controller 5 determines operation parameters for the acceleration operation of the circular accelerator 16 and operation parameters for the beam transport line 2 for transporting the charged particle beam extracted from the circular accelerator 16 to the irradiation nozzle 11, and sends these operation parameters to the accelerator/transportation controller 7.

After completing the preparation for the treatment, the doctor inputs a treatment start signal through the input device of the operation terminal 40.

Upon the input of the treatment start signal, the central controller 5 sends a command signal to the accelerator/transportation controller 7.

Subsequently, the accelerator/transportation controller 7 sets the operation parameters corresponding to the layer to be irradiated first (corresponding to the first beam energy information) to the circular accelerator 16 and the beam transport line 2. Upon completion of the setting of the operation parameters of the circular accelerator 16 and the beam transport line 2 and the preparation for starting the operation (step S30), the scanning magnet power supply controller 8c excites the scanning magnet 11b according to the excitation current parameters (step S31). After the scanning magnet 11b has been excited by the excitation currents corresponding to the first irradiation spot, the dose monitoring controller 8b3 of the monitor monitoring controller 8b starts the monitoring of the beam irradiation dose with reference to the target dose value for the spot position (step S32), by which the irradiation preparation is completed.

When a beam extraction start command is transmitted from the central controller 5 (step S33), the accelerator/transportation controller 7 activates the ion source and thereby generates charged particles (protons or heavy particles). The LINAC 15 accelerates the charged particles supplied from the ion source and outputs the accelerated charged particle beam to the circular accelerator 16. The circular accelerator 16 further accelerates the charged particle beam. The charged particle beam circulating in the circular accelerator 16 is accelerated to a target energy level and then extracted from the circular accelerator 16 to the beam transport line 2. The charged particle beam reaches the scanning irradiation device 3 via the beam transport line 2, propagates inside the irradiation nozzle 11 along the beam axis, and passes through the upstream beam monitor 11a, the scanning magnet 11b, the dose monitor 11c and the downstream beam monitor 11d. The charged particle beam emitted from the irradiation nozzle 11 is applied to the affected part in the patient 13.

The dose monitoring controller 8b3 receives measurement data from the dose monitor 11c, performs a calculation process on the measurement data, and thereby obtains the dose value of the irradiation spot. The irradiation with the charged particle beam is continued until the dose value of the first irradiation spot reaches the target dose value. When the dose value is judged to have reached the target dose value, the dose monitoring controller 8b3 outputs an irradiation achievement signal to the central controller 5 (step S34). The central controller 5 receiving the irradiation achievement signal stops the extraction of the charged particle beam (step S35).

Subsequently, first detection data from the upstream beam monitor 11a is loaded into the upstream beam monitor monitoring controller 8b1, while second detection data from the downstream beam monitor 11d is loaded into the downstream beam monitor monitoring controller 8b2. By using the loaded data, the position and the beam width of the charged particle beam used for the irradiation are calculated (step S36).

After the calculation processing, if there is no abnormality in the beam position or the beam width (if the beam position is judged to be within a permissible beam position range and the beam width is judged to be within a permissible beam width range), a judgment is made on whether or not the irradiation spot for which the irradiation has been completed is the final irradiation spot (final spot position) in the layer. If the irradiation spot is judged not to be the final irradiation spot (No), the process returns to the step S31 and the scanning magnet power supply controller 8c changes the excitation current values of the scanning magnet 11b so as to apply the charged particle beam to the next spot.

After the scanning magnet 11b is excited according to the excitation current parameters set by the scanning magnet power supply controller 8c (step S31), the dose monitoring controller 8b3 of the monitor monitoring controller 8b restarts the monitoring of the beam dose with reference to the target dose value for the next irradiation spot position (step S32). Thereafter, the charged particle beam irradiation for the next irradiation spot position is started when the beam extraction start command is transmitted from the central controller 5 (step S33).

The above control flow (step S37) from the scanning magnet setting (step S31) to the judgment on the final spot is repeated until the irradiation spot for which the irradiation has been completed is judged to be the final spot position in the layer (Yes).

After completing the irradiation of all the spots in the layer, the central controller 5 judges whether or not the layer for which the irradiation has been completed is the final layer to be irradiated for the patient 13. If not the final layer (No), the central controller 5 sends a command signal to the accelerator/transportation controller 7. The accelerator/transportation controller 7 sets the operation parameters corresponding to the next layer to be irradiated next to the circular accelerator 16 and the beam transport line 2 and starts the preparation for the next operation (step S30).

The above control flow (step S38) is repeated until the irradiation is completed for all the layers. The treatment is ended when the irradiation is completed for all layers and spots (step S39).

Here, the measurement of the beam position and the beam width performed by a conventional downstream beam monitor monitoring controller (employing a conventional method) will be explained.

In the beam position/width measurement process executed by the downstream beam monitor monitoring controller, the measurement data of all channels of the downstream beam monitor are loaded first. Thereafter, the offset in each channel is subtracted from the measurement data of each channel and then the peak channel is searched for. After finishing the search, the fitting process is executed while excluding data below N % (e.g., 30%) of the output level of the peak channel. Thereafter, the position and the beam width of the charged particle beam used for the irradiation are calculated. Such a process is also executed by the upstream beam monitor monitoring controller.

In the conventional method, the data of all the channels are loaded and processed even though the channels actually necessary for the calculation of the beam position and the beam width are those outputting N % or more of the peak channel output. Therefore, pulse counters in the monitor signal processing device 22 and pulse integration devices in the downstream beam monitor monitoring controller 8b2 had to be provided corresponding to the number of channels. Thus, the conventional method involves a problem in that the number of devices (components) arranged in the monitor system has to be increased correspondingly when the monitor system is configured to have a larger number of channels than before.

The beam monitor system according to this embodiment was invented in order to resolve such a problem. The beam monitor system of this embodiment will be explained below.

First, the configuration of the beam monitor system will be explained.

The beam monitor system according to this embodiment comprises a beam monitor, a monitor signal processing device, and a beam monitor controller. Here, the explanation of the configuration of the beam monitor system will be given referring to FIG. 3 by taking a downstream beam monitor system as an example. Incidentally, an upstream beam monitor system has a configuration similar to the downstream beam monitor system (differing only in the number of channels of the beam monitor), and thus detailed explanation thereof is omitted for brevity.

The downstream beam monitor 11d is connected to the downstream beam monitor monitoring controller 8b2 via the monitor signal processing device 22.

The downstream beam monitor 11d is a beam monitor of the multi-wire ion chamber type. The downstream beam monitor 11d includes an X electrode for detecting the passage position of the charged particle beam in the X direction, a Y electrode for detecting the passage position of the charged particle beam in the Y direction, a high-voltage electrode for applying voltage (voltage application electrode (not shown)), and a voltage/frequency converter (pulse generator) 23.

While this embodiment is explained by using an example in which the X electrode and the Y electrode are arranged in this order from the upstream side in the propagation direction of the charged particle beam, the X electrode and the Y electrode may also be arranged in reverse order.

The X electrode and the Y electrode are charge collection electrode each of which is configured by stretching a plurality of wire electrodes (e.g., tungsten wires) at even intervals. The wire electrodes constituting the X electrode and the Y electrode are arranged on the beam path of the charged particle beam in order to detect the charged particle beam. By applying voltage to the high-voltage electrode, an electric field is generated between the X electrode and the high-voltage electrode and between the Y electrode and the high-voltage electrode. When the charged particle beam passes through the ion chamber, the gas between the high-voltage electrode and the X electrode and the gas between the high-voltage electrode and the Y electrode are ionized and ion pairs are generated. The generated ion pairs are moved by the electric field to the X electrode and the Y electrode and are collected by the wires (hereinafter referred to as "channels"). Therefore, the beam shape 21 can be detected by measuring the amount of electric charge detected by each channel (detected charge quantity of each channel). Further, the barycentric position and the beam width of the beam can be figured out by performing calculation processing on the detected charge quantities of the channels.

The electric charge detected by each channel is inputted to the voltage/frequency converter 23. The voltage/frequency converter 23 converts the received electric charge into a pulse signal and then outputs the pulse signal (detection signal) to the monitor signal processing device 22.

The monitor signal processing device 22, including two pulse counters 22a, receives and processes the input pulse signal (signal processing). Specifically, each pulse counter of the monitor signal processing device 22 integrates the number of pulses (pulse count) according to the input pulse signal and outputs the integrated pulse count to a pulse integration device (integration pulse counter loading device) 8b2-1 of the downstream beam monitor monitoring controller 8b2. The downstream beam monitor monitoring controller 8b2 includes two pulse integration devices (a first pulse integration device and a second pulse integration device).

The first pulse integration device is connected to the pulse counter connected to the X electrode. The first pulse integration device collects data of the pulse counts according to the signals detected by the X electrode and thereby determines the beam position and the beam width of the charged particle beam in the X-axis direction. Meanwhile, the second pulse integration device is connected to the pulse counter connected to the Y electrode. The second pulse integration device collects data of the pulse counts according to the signals detected by the Y electrode and thereby determines the beam position and the beam width of the charged particle beam in the Y-axis direction. The first pulse integration device and the second pulse integration device are connected to a CPU 8b2-2 in the downstream beam monitor monitoring controller 8b2.

Data regarding the beam position and the beam width determined by the first pulse integration device and the second pulse integration device by the data collection (processing signals) are loaded into the CPU. Based on the processing signals, the CPU calculates the beam shape, the beam barycentric position and the beam width of the charged particle beam that passed through the wire electrodes.

Here, the "beam shape" of the charged particle beam means the intensity distribution of the beam in a plane (X-Y plane) orthogonal to the beam path of the charged particle beam.

The downstream beam monitor monitoring controller 8b2 may also determine the X-axis direction beam shape (beam shape in the X-axis direction) of the charged particle beam that passed through the X electrode based on the processing signals deriving from the detection signals from the X electrode. The downstream beam monitor monitoring controller 8b2 may also determine the Y-axis direction beam shape (beam shape in the Y-axis direction) of the charged particle beam that passed through the Y electrode based on the processing signals deriving from the detection signals from the Y electrode.

While the downstream beam monitor monitoring controller 8b2 in this embodiment is configured to determine the beam shape in the X-axis direction and the beam shape in the Y-axis direction, the configuration of the downstream beam monitor monitoring controller 8b2 is not restricted to this example. For example, the downstream beam monitor monitoring controller 8b2 may also be configured so that the first pulse integration device determines the X-axis direction beam shape (beam shape in the X-axis direction) of the charged particle beam that passed through the X electrode based on the detection signals from the X electrode and the second pulse integration device determines the Y-axis direction beam shape (beam shape in the Y-axis direction) of the charged particle beam that passed through the Y electrode based on the detection signals from the Y electrode.

In this case, the downstream beam monitor monitoring controller 8b2 determines the beam shape in the X-Y plane based on information on the beam shape in the X-axis direction supplied from the first pulse integration device and information on the beam shape in the Y-axis direction supplied from the second pulse integration device.

Next, a method for measuring the beam position and the beam width by use of the downstream beam monitor system of this embodiment will be explained below referring to FIGS. 5-14.

Figure 5:
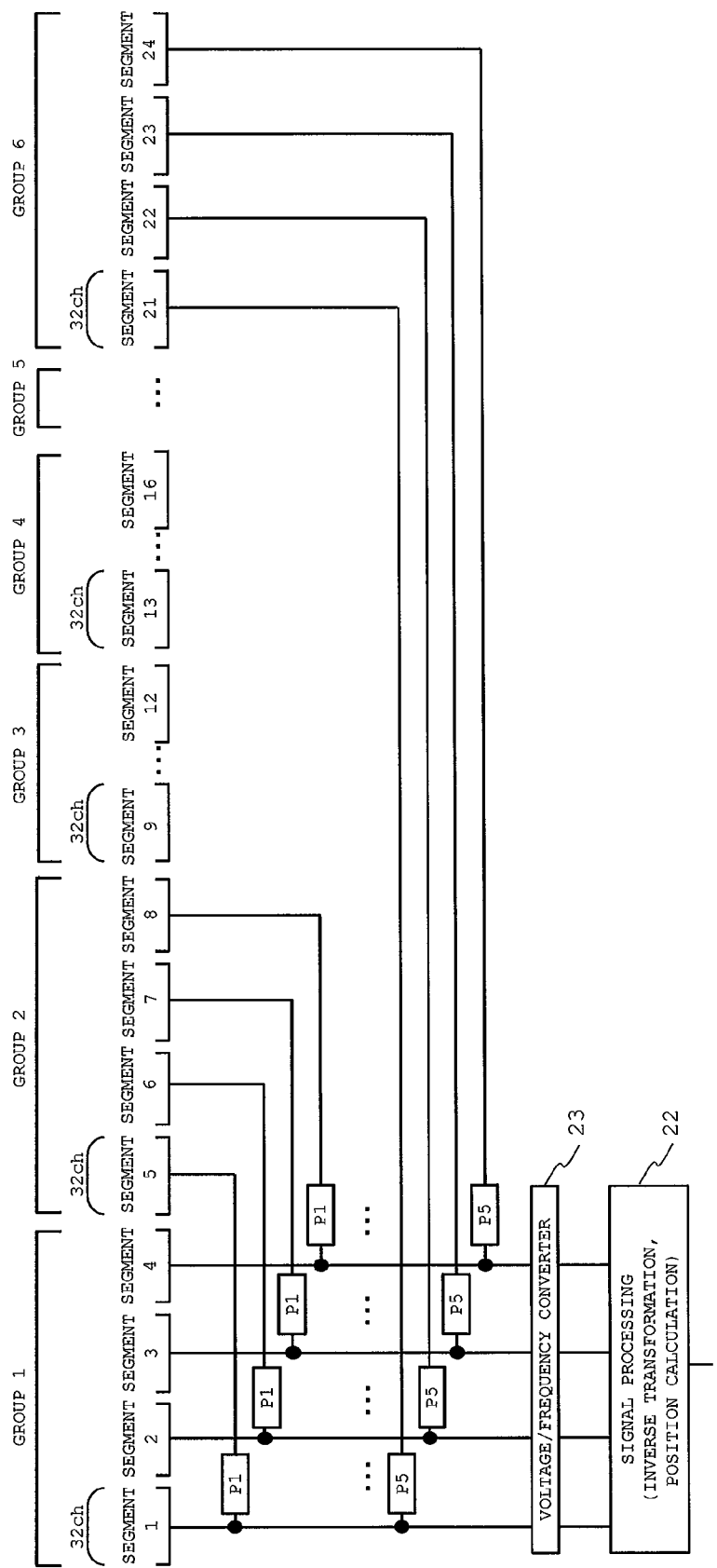
FIG. 5 is a schematic diagram showing an example of channel grouping connection in the beam monitor system according to the first embodiment of the present invention.
Figure 6:
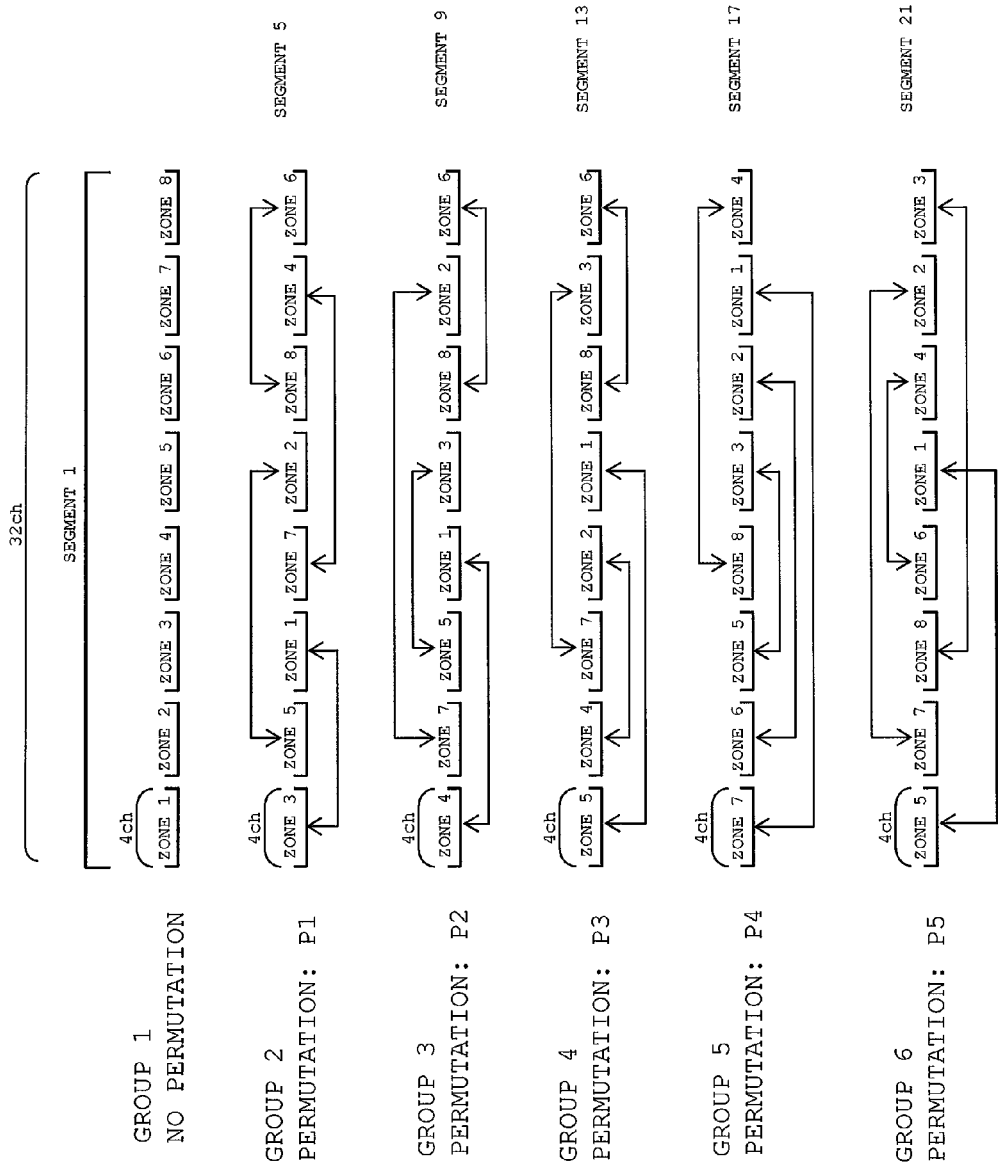
FIG. 6 is a schematic diagram showing an example of permutation connection in the beam monitor system according to the first embodiment of the present invention.
Figure 7:
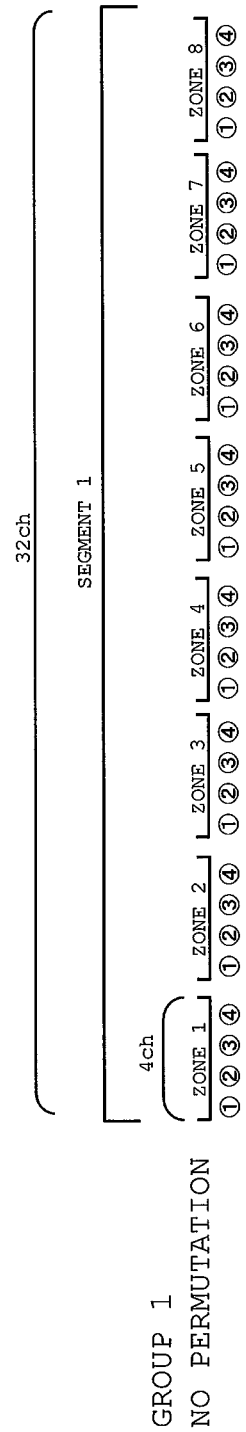
FIG. 7 is a schematic diagram showing an example of the permutation connection in the beam monitor system according to the first embodiment of the present invention.
Figure 8:
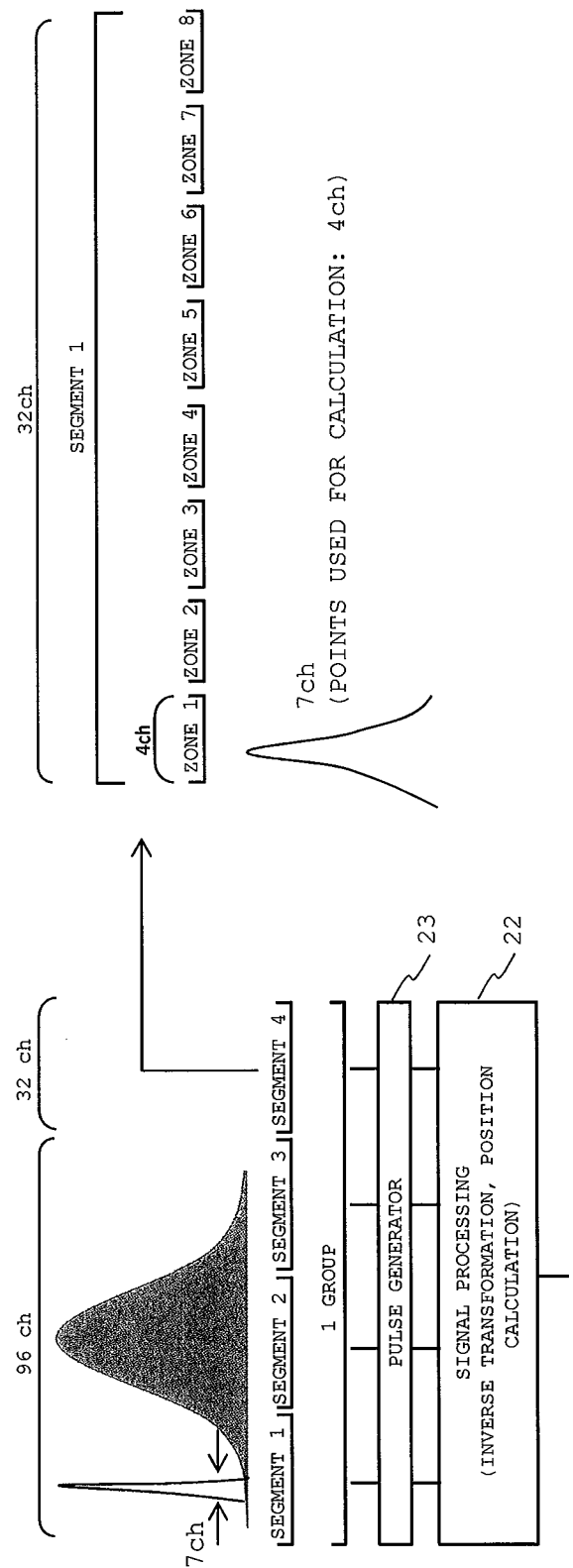
FIG. 8 is a schematic diagram showing the outline of a channel grouping monitor system in the beam monitor system according to the first embodiment of the present invention.
Figure 9:
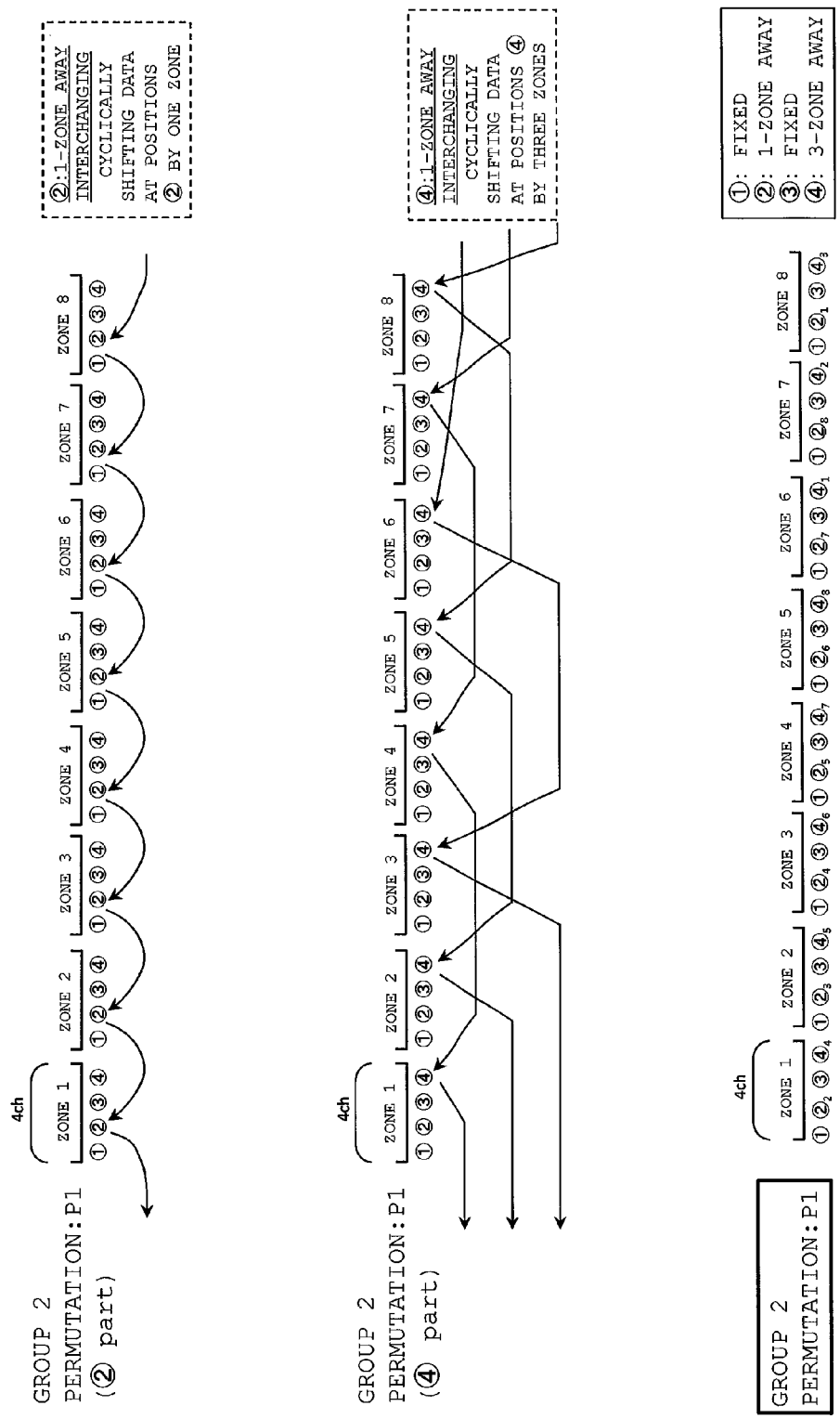
FIG. 9 is a schematic diagram showing an example of the permutation connection in the beam monitor system according to the first embodiment of the present invention.
Figure 10:
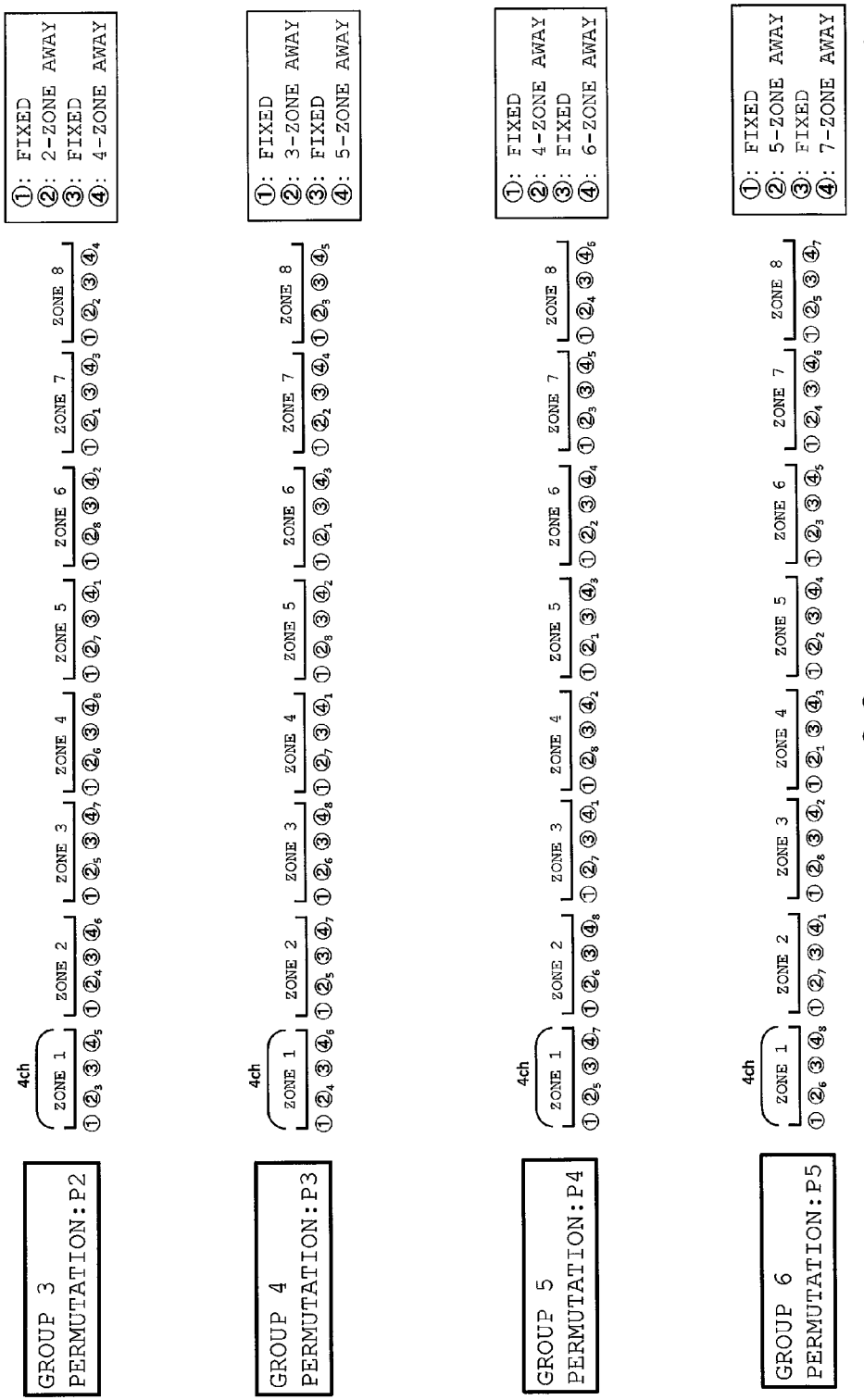
FIG. 10 is a schematic diagram showing an example of the permutation connection in the beam monitor system according to the first embodiment of the present invention.
Figure 11:
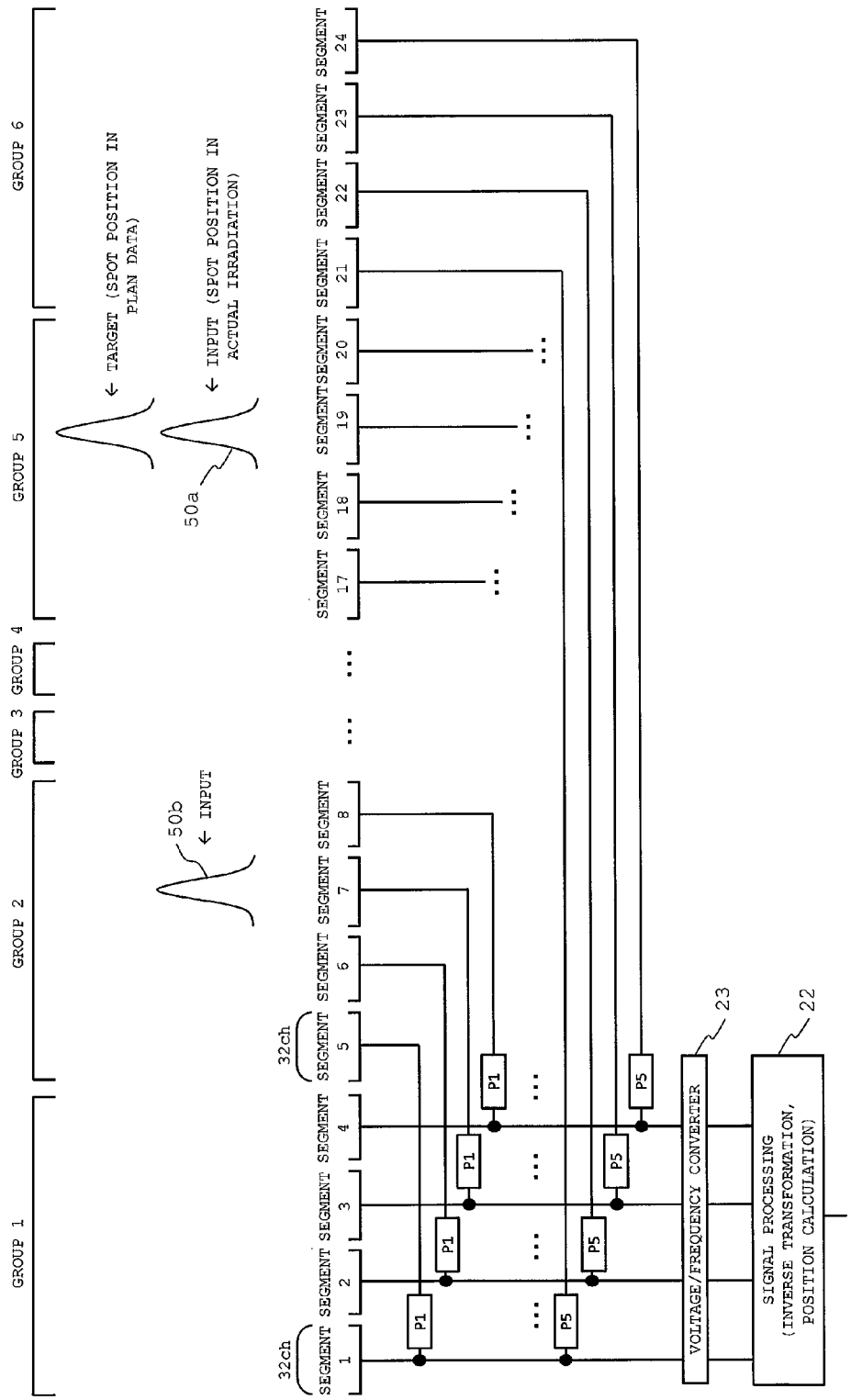
FIG. 11 is a schematic diagram showing the outline of the channel grouping monitor system in the beam monitor system according to the first embodiment of the present invention.
Figure 12:
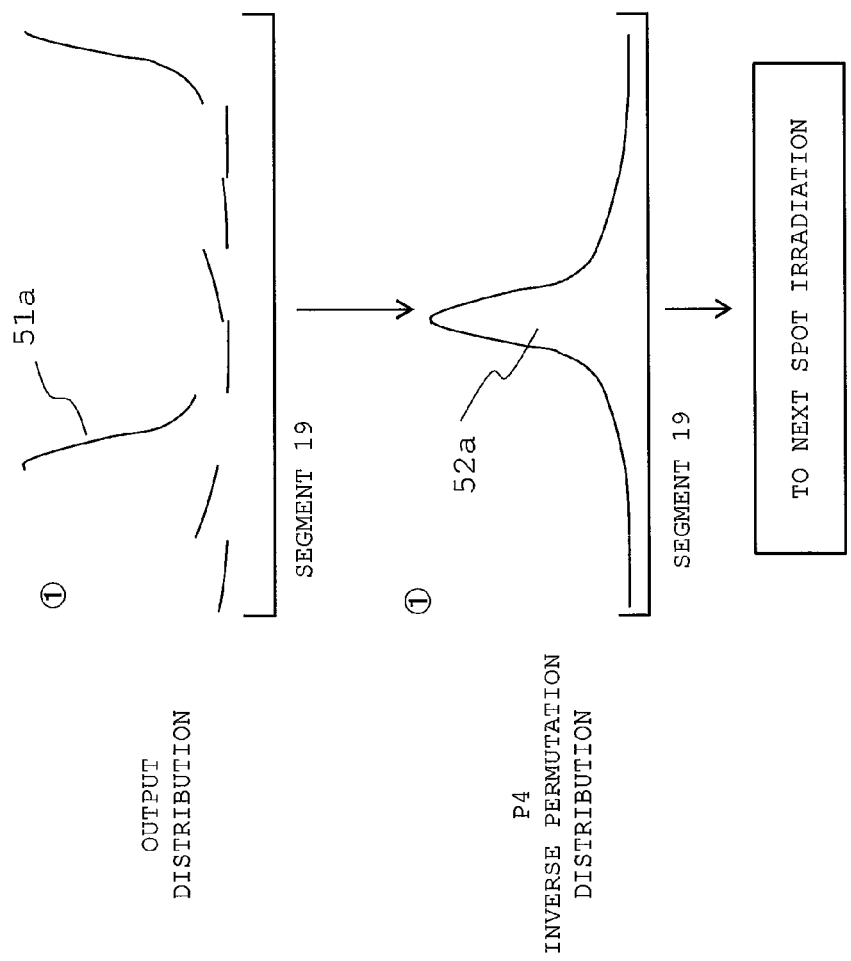
FIG. 12 is a schematic diagram showing output distribution of the channel grouping monitor system in normal times in the beam monitor system according to the first embodiment of the present invention.
Figure 13:
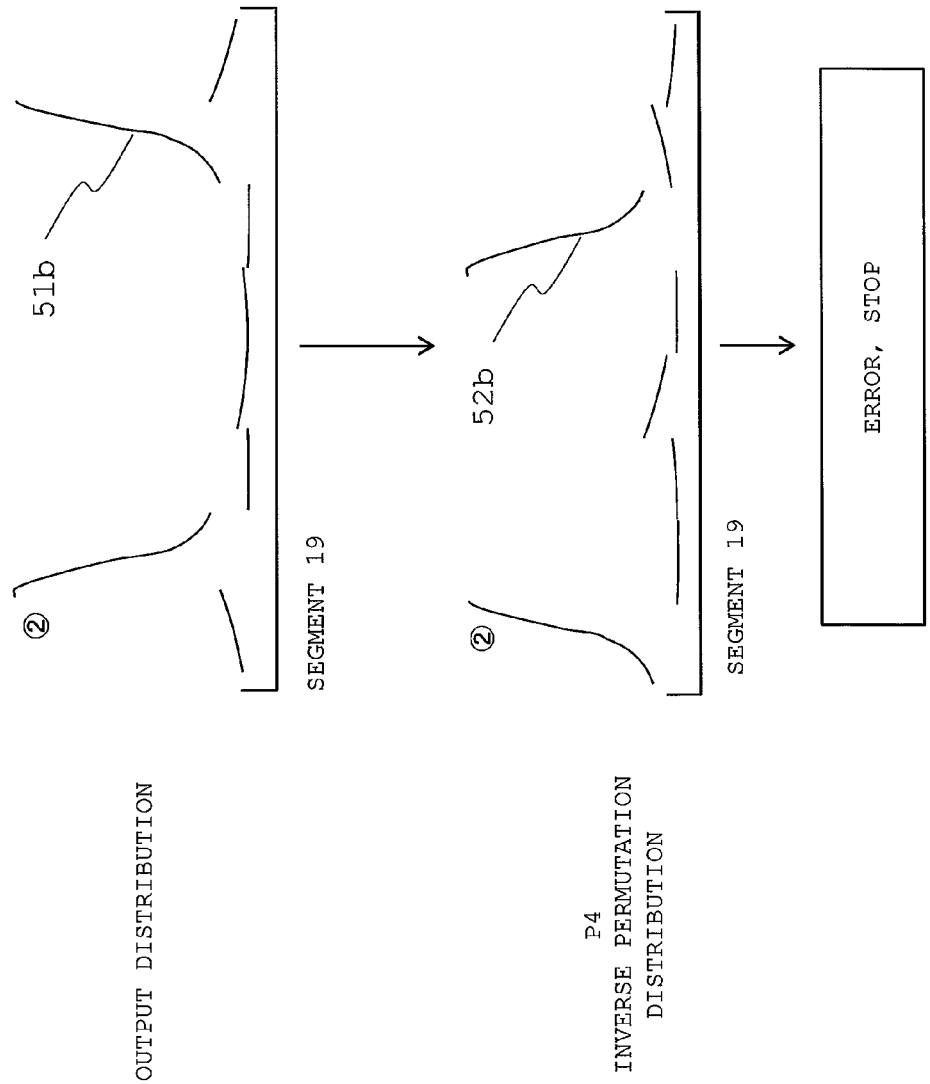
FIG. 13 is a schematic diagram showing output distribution of the channel grouping monitor system in abnormal times in the beam monitor system according to the first embodiment of the present invention.
Figure 14:
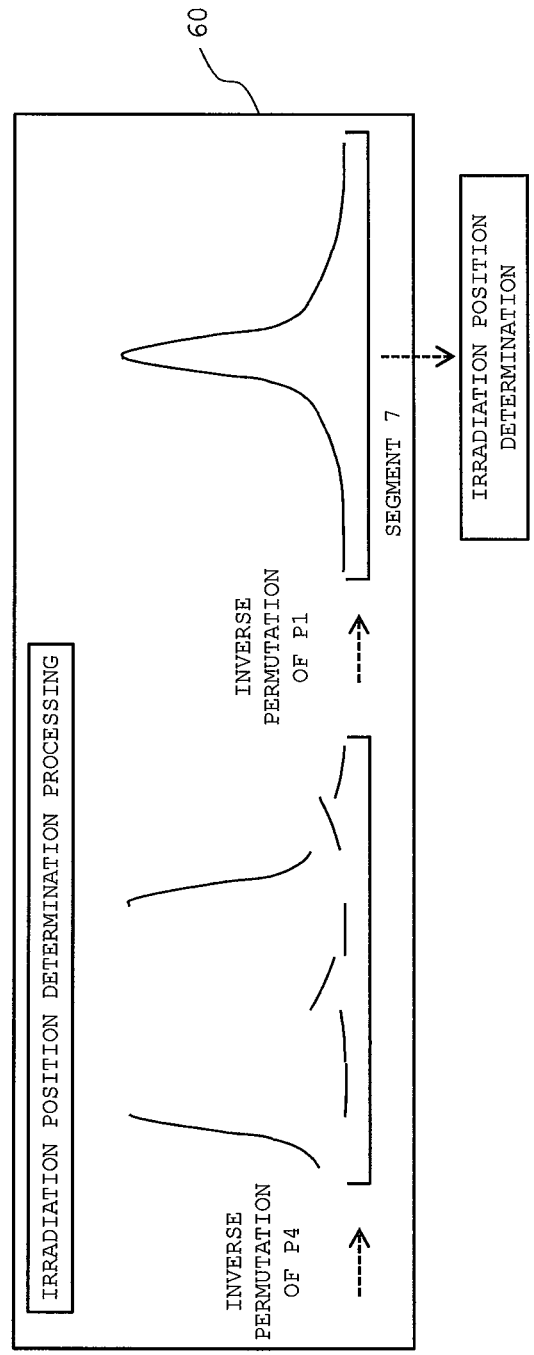
FIG. 14 is a conceptual diagram showing the determination of the irradiation position in abnormal times by the channel grouping monitor system in the beam monitor system according to the first embodiment of the present invention.

FIG. 5 is a schematic diagram showing an example of channel grouping connection in the beam monitor system according to the first embodiment of the present invention. FIG. 6 is a schematic diagram showing an example of permutation connection in the beam monitor system according to the first embodiment of the present invention. FIG. 7 is a schematic diagram showing an example of the permutation connection in the beam monitor system according to the first embodiment of the present invention. FIG. 8 is a schematic diagram showing the outline of a channel grouping monitor system in the beam monitor system according to the first embodiment of the present invention. FIG. 9 is a schematic diagram showing an example of the permutation connection in the beam monitor system according to the first embodiment of the present invention. FIG. 10 is a schematic diagram showing an example of the permutation connection in the beam monitor system according to the first embodiment of the present invention. FIG. 11 is a schematic diagram showing the outline of the channel grouping monitor system in the beam monitor system according to the first embodiment of the present invention. FIG. 12 is a schematic diagram showing output distribution of the channel grouping monitor system in normal times in the beam monitor system according to the first embodiment of the present invention. FIG. 13 is a schematic diagram showing output distribution of the channel grouping monitor system in abnormal times in the beam monitor system according to the first embodiment of the present invention. FIG. 14 is a conceptual diagram showing the determination of the irradiation position in abnormal times by the channel grouping monitor system in the beam monitor system according to the first embodiment of the present invention.

As shown in FIG. 3, the downstream beam monitor 11d in this embodiment includes an X-axis beam monitor 11d1 having the X electrode and the voltage/frequency converter 23 and a Y-axis beam monitor 11d2 having the Y electrode and the voltage/frequency converter 23. The configuration from the X-axis beam monitor 11d1 to the signal processing device 22 is equivalent to that in the Y-axis beam monitor 11d2, and thus the following explanation will be given by taking the X-axis beam monitor 11d1 as an example. The X-axis beam monitor 11d1 is assumed to have 768 wire electrodes (in the X electrode) stretched at even intervals (768 channels), for example.

As shown in FIG. 5, all the channels are divided in units of 32 adjoining channels (32ch) into 24 segments (segment 1-segment 24). Thus, the X-axis beam monitor 11d1 is formed of a plurality of segments (24 segments in this embodiment) each of which includes a plurality of adjoining wire electrodes (32 wire electrodes (32 channels) in this embodiment). As above, each segment is made up of a plurality of adjoining wire electrodes.

Assuming that the wire electrodes constituting the X-axis beam monitor 11d1 are numbered in series as channels 1, 2, 3, 4, . . . , 768 from the edge according to the physical arrangement (order) in regard to the installation position, the segment 1 is made up of the channels 1-32, the segment 2 is made up of the channels 33-64, . . . , the segment 23 is made up of the channels 705-736, and the segment 24 is made up of the channels 737-768.

Further, in this embodiment, four adjoining segments are regarded as one group. Specifically, the segments 1-4 belong to group 1, the segments 5-8 belong to group 2, the segments 9-12 belong to group 3, the segments 13-16 belong to group 4, the segments 17-20 belong to group 5, and the segments 21-24 belong to group 6. It is assumed in this example that each group is formed so that the width from one edge to the other edge of the wire electrodes forming the group is greater than the beam width of the charged particle beam to be used for the irradiation and the beam distribution necessary for the calculation of the beam position and the beam width appears within (M−1) segments (M: the number of segments in one group).

Referring to FIG. 5, the channels (1ch-128ch) in the segments 1-4 belonging to the group 1 are connected to the voltage/frequency converter 23. The signal processing device 22, having the same number of pulse counters as the voltage/frequency converter 23, is connected to the pulse integration devices of the downstream beam monitor monitoring controller 8b2. The signal processing device 22 has as many pulse counters (256 pulse counters in this embodiment) as the sum of the number of wire electrodes belonging to a group in the X-axis beam monitor 11d1 (128 in this embodiment) and the number of wire electrodes belonging to a group in the Y-axis beam monitor $11d2$ (128 in this embodiment). The signal processing device 22 is connected with the voltage/frequency converter 23 by as many lines as the wire electrodes belonging to one group so that each detection signal outputted from a wire electrode selected from each group constituting the X-axis beam monitor $11d1$ is inputted to one input point of the voltage/frequency converter 23 via the same line. As above, the voltage/frequency converter 23 and the signal processing device 22 are only required to be capable of processing all signals of the group 1 (128ch× 2).

The connection method in this embodiment will be explained below. As shown in FIG. 5, each wire electrode in a segment in a group is connected to the signal processing device 22 via the voltage/frequency converter 23 by using the same line as a wire electrode in a segment in each of the other groups.

For example, each wire electrode constituting 129ch-160ch of the segment 5 belonging to the group 2 is connected with one of the wire electrodes constituting 1ch-32ch of the segment 1. Each wire electrode constituting 257ch-288ch of the segment 9 belonging to the group 3 is connected with one of the wire electrodes constituting 1ch-32ch of the segment 1. Each wire electrode constituting 385ch-416ch of the segment 13 belonging to the group 4 is connected with one of the wire electrodes constituting 1ch-32ch of the segment 1. Each wire electrode constituting 513ch-544ch of the segment 17 belonging to the group 5 is connected with one of the wire electrodes constituting 1ch-32ch of the segment 1. Each wire electrode constituting 641ch-672ch of the segment 21 belonging to the group 6 is connected with one of the wire electrodes constituting 1ch-32ch of the segment 1.

Similarly, a wire electrode constituting the segment 2/3/4 of the group 1 is connected with a wire electrode constituting the segment 6/7/8 of the group 2, a wire electrode constituting the segment 10/11/12 of the group 3, a wire electrode constituting the segment 14/15/16 of the group 4, a wire electrode constituting the segment 18/19/20 of the group 5, and a wire electrode constituting the segment 22/23/24 of the group 6.

By connecting wire electrodes of multiple groups together as above, wire electrodes each selected from each group (total of L wire electrodes (L: the number of groups)) are connected to one input point of the voltage/frequency converter 23.

Further, in the above example, the inter-group connection of segments is made according to the order of physical arrangement of the segments (e.g., the segment 5 of the group 2, the segment 9 of the group 3, . . . , and the segment 22 of the group 6 are connected to the segment 1 of the group 1) and the width of the beam distribution is limited within (M−1) segments (M: the number of segments in one group). Such a configuration makes it possible to prevent the measurement data (inputted to the voltage/frequency converter 23) from overlapping with other measurement data in cases of beam irradiation across multiple groups.

In this case, the connection of wire electrodes in each segment is made according to arrangement unique to each group (differently from the physical arrangement in the segment), by which the beam distribution shape measured by the wire electrodes can be shaped (transformed) into a distribution shape unique to each group at the input points of the voltage/frequency converter 23. This makes it possible to judge which wire electrode group underwent the beam irradiation based on the distribution shape. The details of this connection method will be explained below.

For example, 129ch-160ch of the segment 5 are connected to 1ch-32ch of the segment 1. In this case, the connection of the channels of the segment 5 is made by permuting their peers (other ends of connection) according to permutation connection P1 as shown in FIG. 5. Similarly, the channels of the segments 6/7/8 belonging to the same group 2 are also connected to the channels of the segments 2/3/4 by use of the permutation connection P1.

The segment 9 in the group 3 is connected to the channels of the segment 1 by use of permutation connection P2 which is different from the permutation connection P1. Similarly, the channels of the segments 10/11/12 are also connected to the channels of the segments 2/3/4 by use of the permutation connection P2.

The segments 13, 14, 15 and 16 in the group 4 are respectively connected to the segments 1, 2, 3 and 4 in the group 1 by use of permutation connection P3 which is different from the permutation connections P1 and P2. The segments 17, 18, 19 and 20 in the group 5 are respectively connected to the segments 1, 2, 3 and 4 in the group 1 by use of permutation connection P4 which is different from the permutation connections P1, P2 and P3. The segments 21, 22, 23 and 24 in the group 6 are respectively connected to the segments 1, 2, 3 and 4 in the group 1 by use of permutation connection P5 which is different from the permutation connections P1, P2, P3 and P4.

As above, the wire electrodes belonging to a certain segment in a group are connected with wire electrodes belonging to a segment in each of the other groups by use of permutation connection that varies from group to group.

Next, an example of the contents of the permutation connections P1-P5 will be explained below by referring to FIGS. 6-10. An example of employing the permutation connections will be described below assuming that each segment includes 32 channels and each zone includes 4 channels.

First, as shown in FIG. 6, each segment is divided into a plurality of zones. For example, the segment 1 is divided into zones 1-8. Similarly, each of the segments 2-24 is also divided into zones 1-8. Permutation is executed in units of zones by interchanging zones.

For example, the permutation connection P1 is permutation that interchanges the zones 1 and 3, the zones 2 and 5, the zones 4 and 7, and the zones 6 and 8. The permutation connection P2 is permutation that interchanges the zones 1 and 4, the zones 2 and 7, the zones 3 and 5, and the zones 6 and 8. The permutation connection P3 is permutation that interchanges the zones 1 and 5, the zones 2 and 4, the zones 3 and 7, and the zones 6 and 8. The permutation connection P4 is permutation that interchanges the zones 1 and 7, the zones 2 and 6, the zones 3 and 5, and the zones 4 and 8. The permutation connection P5 is permutation that interchanges the zones 1 and 5, the zones 2 and 7, the zones 3 and 8, and the zones 4 and 6.

Further, in this embodiment, in regard to the segment/zone configuration at the measurement position, the channels in each zone are numbered as (1)-(4) (from the channel having the smallest channel number in the zone) as shown in FIGS. 7-10.

First, for the group 1, no permutation connection is executed as shown in FIG. 7 indicating the connection configuration for the group 1. Consequently, the result of the connection is identical with the channel arrangement at the measurement point.

In a case where the beam width of the charged particle beam is narrow (approximately 7 channels) as shown in FIG. 8, the low output level portions on both sides of the Gaussian distribution might be neglected in the calculation process due to truncation, and the number of beam measurement channels necessary for the position measurement width can be within one zone (four channels). In such cases, the beam shape does not break even if inverse permutations for measurement point groups different from the irradiated group (group irradiated by the beam) are executed. Thus, it is difficult to judge which group was irradiated by the beam (i.e., difficult to determine the group that underwent the beam irradiation) based on the distribution shape inputted to the downstream beam monitor monitoring controller $8b2$ via the voltage/frequency converter 23 and the signal processing device 22. To avoid this problem, it is necessary not only to perform the interchanging in units of zones but also to perform permutation on the channels in each zone. Further, considering the fact that the Gaussian fitting can also be calculated by use of three channels (minimum number of necessary channels), it is sufficient if the output values of three channels are separate from one another (separate points), that is, no two adjoining channels are continuous.

Since it is sufficient if adjoining channels differ between the arrangement before the permutation and the arrangement after the permutation as explained above, different types of (cyclic) permutations are performed respectively on the points ch(1), ch(2), ch(3) and ch(4) as indicated in FIG. 9 (showing the case of the group 2) when the dividing into zones in units of four channels is carried out.

Concretely, for the segments 5-8 in the group 2, permutation connection of the type shown in FIG. 9 is used as explained below. In regard to the channel numbers (1)-(4) numbered at the measurement point, the following type of permutation connection is employed: For odd numbers, no permutation is executed (the result of the connection is identical with the channel arrangement at the measurement point). For even numbers, channels having the same channel number in the zones are cyclically interchanged inside the same (each) segment.

Specifically, for the channel number (2), each point (channel having that channel number) is cyclically interchanged with a corresponding point in an adjacent zone (data at the positions (2) are cyclically shifted by one zone). For the channel number (4), each point (channel having that channel number) is cyclically interchanged with a corresponding point in a zone that is 3 zones away ("3-zone away" zone), that is, data at the positions (4) are cyclically shifted by three zones. Consequently, the relationship between the channel arrangements before and after the permutation is: (1) fixed, (2) 1-zone away, (3) fixed, and (4) 3-zone away.

Also for the other groups such as the groups 3 and 4, (cyclic) permutations like those employed for the group 2 (allowing the wire connection in each group to be independent of those in other groups) are employ.

For example, as shown in FIG. 10, for the segments 9-12 in the group 3, (cyclic) permutation causing channel arrangement relationship (1) fixed, (2) 2-zone away, (3) fixed, and (4) 4-zone away is employed. For the segments 13-16 in the group 4, (cyclic) permutation causing channel arrangement relationship (1) fixed, (2) 3-zone away, (3) fixed, and (4) 5-zone away is employed. For the segments 17-20 in the group 5, (cyclic) permutation causing channel arrangement relationship (1) fixed, (2) 4-zone away, (3) fixed, and (4) 6-zone away is employed. For the segments 21-24 in the group 6, (cyclic) permutation causing channel arrangement relationship (1) fixed, (2) 5-zone away, (3) fixed, and (4) 7-zone away is employed.

Consequently, the wire electrodes are connected to the channels of the voltage/frequency converter 23 so that no two adjoining channels (among the four consecutive measurement channels in each zone) become physically continuous.

In FIGS. 9 and 10, the subscripts attached to (2) and (4) correspond to the zone number before the (cyclic) permutation.

Next, the operation in this embodiment will be explained below.

Upon receiving the detection signals from wire electrodes, the signal processing device 22 determines group information which indicates to which group the wire electrodes that sent the inputted detection signals belong (i.e., which group includes the wire electrodes that sent the inputted detection signals). Further, the signal processing device 22 determines the beam shape of the charged particle beam that passed through the wire electrodes by rearranging (inversely permuting) the detection signals based on the information on the permutation connection. The signal processing device 22 sends a processing signal including the determined group information and beam shape information to the CPU $8b2$-2 of the downstream beam monitor monitoring controller $8b2$ via the pulse integration device $8b2$-1. It is also possible to have a data storage device of the signal processing device 22 store the received detection signals, process the stored detection signals, and send out the processing signal as the result of the processing. Based on the received beam shape information and group information, the downstream beam monitor monitoring controller $8b2$ determines the beam position and the beam width of the charged particle beam that passed through the wire electrodes. Then, the downstream beam monitor monitoring controller $8b2$ has the determined beam position and beam width displayed on the display screen of the operation terminal 40.

Referring to FIG. 11, a case where the beam irradiation has been successfully performed exactly on the target determined by the treatment planning device 6 (normal time $50a$) will be considered first.

In a case where the segment 19 was irradiated by the beam, the values detected in the segment 19 are permutated by use of the permutation connection P4, connected to the segment 3, and sent to the voltage/frequency converter 23. The output distribution in this case is illustrated as the output distribution $51a$ (normal time) in FIG. 12, in which no Gaussian distribution is acquired due to the effect of the permutation P4. Incidentally, in regard to the in-zone cyclic permutations, an example after the inverse transformation is shown in FIG. 12 for the sake of easy understanding.

However, since the position to be irradiated with the beam has already been determined by the treatment planning device 6, it is possible to estimate which one of the permutation connections P1-P5 was performed on the actual irradiating beam based on the treatment plan data generated by the treatment planning device 6.

Since the segment 19 has been determined as the planned target position in this embodiment, it can be estimated that the permutation was performed by means of the permutation connection P4. Thus, by having the monitor signal processing device 22 execute the inverse permutation of P4, a Gaussian distribution can be acquired as indicated by the inverse permutation distribution (normal time) $52a$. Thanks to the acquisition of the Gaussian distribution, the coincidence of the actual irradiation position with the irradiation position in the treatment plan data becomes clear and the beam position and the beam width can be determined precisely. Further, a low-cost monitor system can be realized since the voltage/frequency converter 23 and the monitor signal processing device 22 are only required to have components corresponding to the number of channels in one group.

Next, a case where the actual beam irradiation position differs from the target irradiation position according to the treatment plan (abnormal time $50b$ in FIG. 11) will be considered below.

For example, a case where the actual beam irradiation position is the segment 7 even though the target irradiation position is the segment 19 will be considered.

In this case, the values detected by the segment 7 are permuted by P1 and then sent to the voltage/frequency converter 23, by which the output distribution (abnormal time) 51b is obtained as shown in FIG. 13. However, since the target irradiation position according to the treatment plan is the segment 19, the monitor signal processing device 22 performs the inverse permutation of P4 on the output, by which the inverse permutation output distribution (abnormal time) 52b is obtained. Consequently, no Gaussian distribution can be acquired.

In this case, the downstream beam monitor monitoring controller 8b2 outputs an error signal representing a beam error (abnormality in the position or width of the beam or incapability of calculation thereof) to the central controller 5. The central controller 5 receiving the error signal outputs a beam stop signal to the accelerator/transportation controller 7 and thereby stops the charged particle beam extracted from the circular accelerator 16.

The downstream beam monitor monitoring controller 8b2 also executes irradiation position determination processing 60 and thereby determines the position of the abnormal irradiation with the charged particle beam.

For example, as shown in FIG. 14, the irradiation position determination processing 60 successively performs inverse permutations (inverse permutation of P1, inverse permutation of P2, . . . ) on the output distribution deriving from the abnormal irradiation and thereby determines a permutation connection capable of acquiring a Gaussian distribution. This processing enables to precisely learn which channel underwent the abnormal irradiation. In this embodiment, a Gaussian distribution is acquired by use of the inverse permutation of P1. This clarifies that a particular channel in the group 2 underwent the abnormal irradiation.

Further, in cases where the beam width changed, it is possible to determine the beam position and the beam width by performing simulation in consideration of permutation connection across arbitrary beam widths within a certain beam width range and comparing the results of the simulation with the actual irradiation distribution.

In this simulation, a process in the actual beam monitor system from the sensor part to the step before the inputting to the pulse generator is simulated on a computer. On the assumption that the actual irradiation distribution at the time of the abnormal irradiation is a Gaussian distribution, the beam position and the beam width at the time of the abnormal irradiation are determined by giving inputs (inputting input values of the beam position and the beam width) while changing the input values between certain values at fixed intervals, comparing each computer output result (obtained by employing the permutation connection determined from the beam position) with the actual irradiation distribution inputted to the signal processing device 22 or the downstream beam monitor monitoring controller, and finding a computer output result that coincides with the actual irradiation distribution.

While the above explanation of this embodiment has been given about the case where the beam fits in one group for the sake of easy understanding, there is also a possibility that the irradiation is performed on a position (part) straddling two or more groups. Also in such cases, the permutation is performed for each segment according to the method unique to the group including the segment. Therefore, by performing the inverse permutation in units of segments based on the permutation information on the group including each segment, precise determination of the beam position and the beam width and the judgment on the normality/abnormality of the beam position and the beam width are possible even for a beam distribution at a position straddling two or more groups.

In the particle beam irradiation system comprising the beam monitor system according to this embodiment, the channels used for the calculation of the position and the beam width of the charged particle beam are limited to a small number in the multi-wire type beam monitor system having a simple configuration in which the wires are grouped into groups and the connection method varying from group to group (unique to each group) is executed. Therefore, it is unnecessary to prepare amplifiers and signal processing devices corresponding to all the channels.

A comparison will be made below between the beam monitor system according to this embodiment and the conventional beam monitor system.

In the conventional beam monitor system, in cases where the X-axis beam monitor is formed of 768 wire electrodes, 768 (=the number of wire electrodes (the number of channels)) pulse generators and pulse counters are arranged after the X-axis beam monitor. Similarly, in cases where the Y-axis beam monitor is formed of 768 wire electrodes, 768 pulse generators and pulse counters are arranged after the X-axis beam monitor. Therefore, the conventional monitor system includes 768 pulse generators and 768 pulse counters.

In contrast to such a conventional monitor system, even when the X-axis beam monitor is formed of as many as 768 wire electrodes, the beam monitor system according to this embodiment is capable of determining the beam position and the beam width of the charged particle beam with a simple configuration of 128 pulse generators and 128 pulse counters (considerably smaller number than the number of wire electrodes (the number of channels)).

In the beam monitor system of this embodiment, the charge collection electrode is formed of a plurality of groups each of which is made up of a plurality of adjoining wire electrodes. Further, all the wire electrodes are connected to the channels of the signal processing device by the same number of lines as the wire electrodes belonging to one group so that each detection signal outputted from one wire electrode selected from each group is inputted through the same line and so that no two adjoining channels are physically continuous in regard to a certain set of consecutive measurement channels. Furthermore, the signal processing device 22 determines the group information (indicating to which group the wire electrodes that sent the inputted detection signals belong) and outputs the processing signal including the group information to the beam monitor controller. Based on the processing signal, the beam monitor controller determines the position and the beam width of the charged particle beam that passed through the wire electrodes.

Thus, the monitor system can be constructed in a simple configuration. Moreover, according to this embodiment, the wire connection method is changed from group to group, by which the irradiation position can be learned precisely and a monitor system with high reliability can be realized.

If the permutation is performed just by simply interchanging zones, the aforementioned problem occurs when a thin beam having a narrow beam width is used for the irradiation and the number of channels necessary for the position/width calculation is within one zone. Since the distribution shape does not change in this case irrespective of the presence/absence and the type of permutation connection, there is a possibility that the beam distribution shape at the measurement position coincides with the beam distribution shape after the permutation connection at the voltage/frequency converter 23 and the erroneously irradiating beam cannot be detected. However, with the permutation connection configuration in this embodiment, even when a thin beam having a beam width of approximately 3 channels (whose beam distribution is barely recognizable) is used for the irradiation, the beam distribution shape at the measurement position is broken by the permutation connection since the wire electrodes are connected by wire (line) to the channels of the signal processing device so that no two adjoining channels are physically continuous in regard to a certain set of consecutive measurement channels. This enables to make the beam distribution at the measurement position necessarily change at the signal processing device 22 in regard to each group and to cause a deviation (error) in the position/width calculation, by which the irradiation at an erroneous position can be detected precisely.

With the above configuration, the monitor system of this embodiment makes it possible to precisely manage the irradiation dose and the irradiation position for each patient.

The particle beam irradiation system comprising the beam monitor system according to this embodiment is especially effective for irradiation methods in which a thin charged particle beam is scanned and applied to the target. In order to perform high-precision irradiation, a small-diameter beam becomes necessary and the number of wires (in unit length) of the multi-wire type monitor for measuring the beam profile increases accordingly. However, wires irradiated by the charged particle beam at the same time are only a small part of all the wires. The beam monitor system of this embodiment is configured to connect a small number of wires corresponding to the irradiation range to other wires, as a system for performing the signal processing exclusively on a small number of wire signals corresponding to the range irradiated by the charged particle beam at the same time. Consequently, a low cost and high reliability can be realized.

The particle beam irradiation system comprising the beam monitor system according to this embodiment changes the wire electrode connection method from group to group. This enables to precisely learn the irradiation position and realize a monitor system with high reliability.

Second Embodiment

A second embodiment of the beam monitor system and the particle beam irradiation system in accordance with the present invention will be described below referring to FIGS. 15 and 16.

Figure 15:
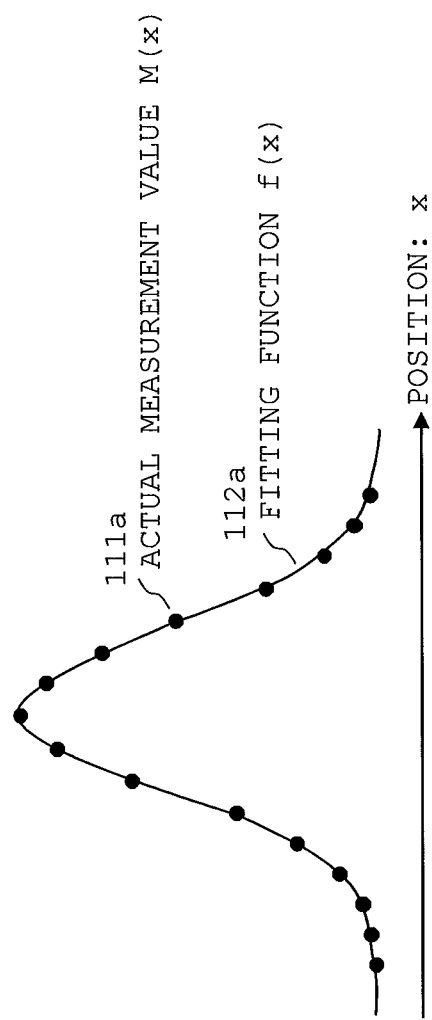
FIG. 15 is a schematic diagram showing an example of a fitting function and the distribution of actual measurement values in a second embodiment of the beam monitor system in accordance with the present invention.

FIG. 15 is a schematic diagram showing an example of the fitting function and the distribution of actual measurement values in the second embodiment of the beam monitor system in accordance with the present invention. FIG. 16 is a schematic diagram showing another example of the fitting function and the distribution of actual measurement values in the second embodiment of the beam monitor system in accordance with the present invention.

In the beam monitor system according to the second embodiment, the upstream beam monitor monitoring controller 8b1 or the downstream beam monitor monitoring controller 8b2 employs another condition (additional condition) for the judgment on the appropriateness of the irradiation in addition to the aforementioned condition that the calculation results of the beam position and the beam width are within the permissible ranges. The additional condition employed in this embodiment is that the mean square of the difference between the fitting function (obtained from the distribution of the measurements) and the actual measurement value of each channel (variance) is within a permissible value.

The configuration of the beam monitor system and the particle beam irradiation system in this embodiment other than the condition for the judgment by the upstream beam monitor monitoring controller 8b1 or the downstream beam monitor monitoring controller 8b2 is substantially equivalent to that in the first embodiment, and thus detailed explanation thereof is omitted for brevity.

Next, the operation in this embodiment will be explained below by taking the downstream beam monitor monitoring controller 8b2 as an example similarly to the first embodiment.

Upon receiving the detection signals from wire electrodes, the signal processing device 22 determines group information which indicates to which group the wire electrodes that sent the inputted detection signals belong. Further, the signal processing device 22 determines the beam shape of the charged particle beam that passed through the wire electrodes by rearranging the detection signals based on the information on the permutation connection. Similarly to the first embodiment, this embodiment may also be configured to make the downstream beam monitor monitoring controller 8b2 carry out this processing.

Based on the received beam shape information, the downstream beam monitor monitoring controller 8b2 determines the beam width of the charged particle beam that passed through the wire electrodes. Based on the received beam shape information and group information, the downstream beam monitor monitoring controller 8b2 determines the beam position of the charged particle beam that passed through the wire electrodes.

Further, in the position/width calculation, the downstream beam monitor monitoring controller 8b2 calculates the mean square of the difference between the fitting function and the actual measurement value (variance).

The variance $\sigma^2$ is calculated according to the following expression (1):

$$\sigma^2 = \frac{1}{n}\sum_{x=1}^{n}(f(x) - M(x))^2 \tag{1}$$

where n represents the number of channels used for the beam position/width calculation, x represents each measurement channel, f(x) represents the fitting function, and M(x) represents the actual measurement value.

Then, the downstream beam monitor monitoring controller 8b2 judges that the irradiation was done at the normal beam position if the variance $\sigma^2$ is within a certain value (permissible value)($\sigma^2 \leq \text{const}$). If the variance $\sigma^2$ is greater than the permissible value, the downstream beam monitor monitoring controller 8b2 judges that the irradiation was done at an abnormal beam position and outputs an error signal representing a beam error to the central controller 5.

Specifically, in the case of the calculation after the inverse permutation at the normal beam position, the actual measurement value 111a after the execution of the inverse permutation by the calculation processing unit appears on or in the vicinity of the fitting function 112a as shown in FIG. 15.

In this case, the difference between the fitting function 112a and the actual measurement value 111a is extremely small and the variance is within the permissible value. Therefore, the downstream beam monitor monitoring controller 8b2 judges that the irradiation was done at the normal beam position and has the determined beam position and beam width displayed on the display screen of the operation terminal 40.

Figure 16:
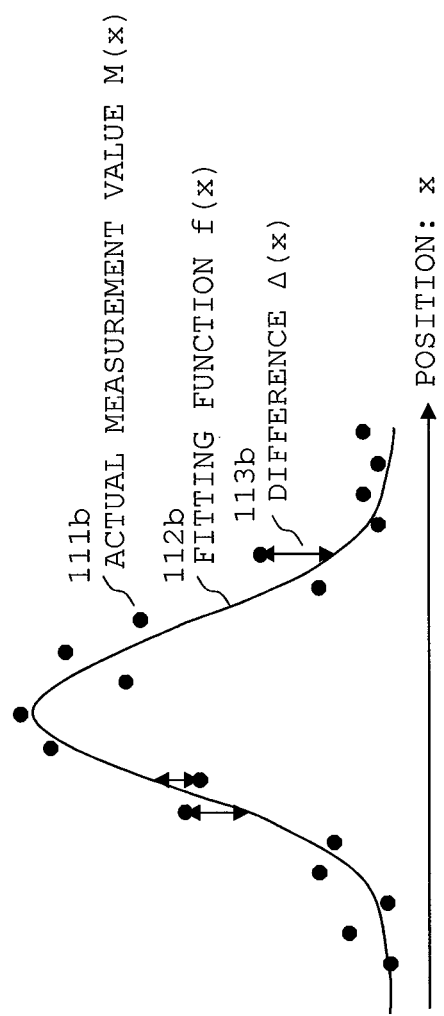
FIG. 16 is a schematic diagram showing another example of the fitting function and the distribution of actual measurement values in the second embodiment of the beam monitor system in accordance with the present invention.

In contrast, in the calculation after the inverse permutation at an erroneous beam position, there are cases where the fitting function 112b closely resembles the function representing the normal beam whereas the distribution of the actual measurement values is rather dispersed as shown in FIG. 16.

In this case, the variance exceeds the permissible value since the deviation of each actual measurement value 111b from the fitting function 112b is great. Thus, the downstream beam monitor monitoring controller 8b2 judges that the irradiation was done at an abnormal beam position and outputs the error signal representing the beam error to the central controller 5. The downstream beam monitor monitoring controller 8b2 also executes the irradiation position determination processing 60.

Also in the second embodiment of the beam monitor system and the particle beam irradiation system in accordance with the present invention, effects substantially equivalent to the aforementioned effects of the first embodiment are achieved.

Thus, the monitor system can be constructed with a simple configuration, and a low-cost and high-reliability monitor system can be realized.

In the case where the permutation wholly interchanging the channels inside each segment in units of some channels (explained in the first embodiment) is executed, it is easily possible to detect erroneous irradiation by checking the distribution shape at the signal processing unit. However, the distribution fitting process has been conducted in the beam position/width calculation. Thus, in the distribution after undergoing the permutation wholly interchanging the channels, even a fitting function for an erroneous beam position can be determined as a function close to the fitting function for the correct beam position depending on the way of the fitting.

In contrast, the judgment on the appropriate irradiation in this embodiment employs the additional condition that the mean square of the difference between the fitting function (obtained from the distribution) and the actual measurement value of each channel (variance) is within a permissible value in addition to the condition that the calculation results of the position and the width are within the permissible ranges. Therefore, the judgment on whether the beam position is appropriate or not can be made more precisely through the evaluation of the deviation of the actual measurement values from the fitting function used for the calculation. Consequently, a monitor system capable of precisely detecting erroneous irradiation by means of calculation can be realized.

Incidentally, while the judgment on the appropriate irradiation (detection of erroneous irradiation) by the signal processing device 22 in this embodiment is made by using the variance as the criterion, the criterion usable for the judgment is not limited to the variance. For example, the absolute value of the difference between the fitting function and the actual measurement value in regard to each channel or the sum of the absolute values of the differences may also be used as the criterion for the judgment.

Third Embodiment

A third embodiment of the beam monitor system and the particle beam irradiation system in accordance with the present invention will be described below referring to FIG. 17.

FIG. 17 is a flow chart of charged particle beam irradiation control according to the raster scan method.

While the particle beam irradiation system in the first embodiment comprises the beam monitor system for monitoring the beam position and the beam width in the spot scanning irradiation, the particle beam irradiation system in this embodiment comprises a beam monitor system for monitoring the beam position and the beam width in the raster scanning irradiation.

In the raster scanning irradiation method, the affected part in the patient 13 is divided into a plurality of layers successively arranged in the beam propagation direction, and the irradiation of each layer is performed by scanning the charged particle beam throughout the layer while continuing the beam irradiation (keeping the beam ON). The beam monitor system of the particle beam irradiation system in this embodiment is configured to monitor the beam position and the beam width in the raster scanning irradiation.

The particle beam irradiation system according to this embodiment will be explained below referring to FIG. 17, mainly about the difference in the configuration and the operation from the first embodiment.

After completing the preparation for the treatment, the doctor inputs the treatment start signal through the input device of the operation terminal 40.

Upon the input of the treatment start signal, the central controller 5 sends the command signal to the accelerator/transportation controller 7.

The accelerator/transportation controller 7 sets the operation parameters corresponding to the layer to be irradiated first (corresponding to the first beam energy information) to the circular accelerator 16 and the beam transport line 2. Upon completion of the setting of the operation parameters of the circular accelerator 16 and the beam transport line 2 and the preparation (step S30), the scanning magnet power supply controller 8c excites the scanning magnet 11b according to the excitation current parameters (step S31A). After the scanning magnet 11b has been excited by the excitation currents corresponding to the first irradiation position, the dose monitoring controller 8b3 of the monitor monitoring controller 8b starts the monitoring of the beam dose with reference to the target dose value for the spot position (step S32A), by which the irradiation preparation is completed.

When the beam extraction start command is transmitted from the central controller 5 (step S33), the accelerator/transportation controller 7 activates the ion source and thereby generates charged particles (protons or heavy particles). The LINAC 15 accelerates the charged particles supplied from the ion source and outputs the accelerated charged particle beam to the circular accelerator 16. The circular accelerator 16 further accelerates the charged particle beam. The charged particle beam circulating in the circular accelerator 16 is accelerated to a target energy level and then extracted from the circular accelerator 16 to the beam transport line 2. The charged particle beam reaches the scanning irradiation device 3 via the beam transport line 2. Further, the charged particle beam propagates inside the irradiation nozzle 11 along the beam axis and passes through the upstream beam monitor 11a, the scanning magnet 11b, the dose monitor 11c and the downstream beam monitor 11d. The charged particle beam emitted from the irradiation nozzle 11 is applied to the affected part in the patient 13.

The dose monitoring controller 8b3 receives measurement data from the dose monitor 11c, performs a calculation process on the measurement data, thereby obtains the dose on the irradiation position (dose value of the irradiation position), and continues the irradiation with the charged particle beam until the dose value of the first irradiation position reaches the target dose value. When the dose value is judged to have reached the target dose value, the dose monitoring controller 8b3 outputs the irradiation achievement signal to the central controller 5 (step S34).

The first detection data from the upstream beam monitor 11a is loaded into the upstream beam monitor monitoring controller 8b1, the second detection data from the downstream beam monitor 11d is loaded into the downstream beam monitor monitoring controller 8b2, and the position and the beam width of the charged particle beam used for the irradiation are calculated by using the loaded data (step S35A). After the calculation processing, if there is no abnormality in the beam position or the beam width (if the beam position is judged to be within the permissible beam position range and the beam width is judged to be within the permissible beam width range), a judgment is made on whether or not the irradiation position for which the irradiation has been completed is the final irradiation position in the layer. If the irradiation position is judged not to be the final irradiation position (No), the scanning magnet power supply controller 8c makes the spot scanning magnet setting based on the excitation current parameters (step S35B), and the monitor monitoring controller 8b makes the spot dose target value setting (step S35C).

Thereafter, the process returns to the step S34 and the above control flow S37A from the dose achievement judgment step S34 to the judgment on the final spot (final position) is repeated until the irradiation spot (irradiation position) for which the irradiation has been completed is judged to be the final spot position in the layer (Yes).

After completing the irradiation of all the spots in the layer, the central controller 5 judges whether or not the layer for which the irradiation has been completed is the final layer to be irradiated for the patient 13 (step S36A). If not the final layer (No), the central controller 5 sends the command signal to the accelerator/transportation controller 7. The accelerator/transportation controller 7 sets the operation parameters corresponding to the next layer (to be irradiated next) to the circular accelerator 16 and the beam transport line 2 and starts the preparation for the next operation (step S30).

The above control flow S38A is repeated until the irradiation is completed for all the layers. The treatment is ended when the irradiation is completed for all layers and spots (step S39).

In the flow described above, the upstream beam monitor monitoring controller 8b1 and the downstream beam monitor monitoring controller 8b2 execute processes similar to those in the first embodiment.

As described above, the particle beam irradiation system in this embodiment implements the raster scanning irradiation method of performing the beam irradiation on the affected part by successively changing the irradiation position while continuing the extraction (emission) of the charged particle beam.

Also in the third embodiment of the beam monitor system and the particle beam irradiation system in accordance with the present invention, effects substantially equivalent to the aforementioned effects of the first embodiment are achieved.

Thus, the monitor system can be constructed with a simple configuration, and a low-cost and high-reliability monitor system can be realized.

Incidentally, the particle beam irradiation system according to this embodiment is applicable also to the particle beam irradiation system comprising the beam monitor system monitoring the beam position and the beam width according to the second embodiment.

Other Examples

The present invention is not to be restricted to the above embodiments; a variety of modifications and applications are possible.

For example, the numbers of the channels, segments and groups constituting each monitor may be set arbitrarily according to design requirements or the like. While the permutation connection in the above embodiments is performed on the channels in each zone by performing no permutation connection on odd-numbered channels and performing (cyclic) permutation connection on each even-numbered channel, the permutation connection may be executed in an arbitrary connection method as long as the wire connection is made to the channels of the signal processing unit so that no two adjoining channels are physically continuous in regard to a certain set of consecutive measurement channels.

The above embodiments have been explained in detail as particular illustrative examples for easy understanding of the present invention, and thus embodiments of the present invention are not restricted to those including all the configurations or features explained above.

For example, while the signal processing device in the above embodiments is implemented by a digital monitor signal processing device including the voltage/frequency converter and the pulse counter, the signal processing device may also be implemented by a circuit which integrates the electric charge, converts the electric charge into voltage, and outputs the voltage or an analog monitor signal processing device which converts electric current into voltage and outputs the voltage.

The numbers of the channels, segments and groups constituting each monitor may be set arbitrarily, and the permutation connection inside each group does not need to be the same.

While the permutation connection in the above embodiments is executed by permutation by interchanging zones after dividing each segment into a plurality of zones, the method of the permutation connection is not restricted to the above examples; the permutation connection may be executed in arbitrary permutation methods.

While the signal processing device and the beam monitor controller are installed in separate devices in the above embodiments, it is also possible to install the signal processing device and the beam monitor controller in the same device.

What is claimed is:

1. A beam monitor system comprising a collection electrode for detecting a charged particle beam passing therethrough, a signal processing device, and a beam monitor controller, wherein:
   the collection electrode includes a plurality of groups each of which is made up of a plurality of adjoining wire electrodes and divided into segments each including a plurality of adjoining wire electrodes, and
   each wire electrode in a segment in a group is connected to the signal processing device by using the same line as a wire electrode in a segment in each of the other groups, and
   the wire electrodes in each segment in each of the other groups are connected to the signal processing device by employing permutation connection varying from group to group so that no two adjoining channels are physically continuous, and
   the signal processing device rearranges detection signals outputted from the wire electrodes based on information related to a planned beam irradiation target position and information on the permutation connection and outputs the result of the rearrangement as a processing signal, and the beam monitor controller calculates the beam position and the beam width of the charged particle beam that passed through the wire electrodes based on the processing signal outputted from the signal processing device.

2. The beam monitor system according to claim 1, wherein the beam monitor controller judges whether deviation between a fitting function of beam distribution determined from the processing signal from the signal processing device and the actual measurement value in regard to each channel is within a permissible value or not, judges that appropriate irradiation has been performed if the deviation is judged to be within the permissible value, and judges that inappropriate irradiation has been performed and outputs a warning signal if the deviation is judged to be greater than the permissible value.

3. The beam monitor system according to claim 2, wherein the beam monitor controller calculates at least one selected from the absolute value of the difference between the fitting function and the actual measurement value, the sum of the absolute values of the differences, and the mean square of the differences as the deviation between the fitting function of beam distribution determined from the processing signal from the signal processing device and the actual measurement value in regard to each channel.

4. A particle beam irradiation system comprising the beam monitor system according to claim 3.

5. A particle beam irradiation system comprising the beam monitor system according to claim 2.

6. A particle beam irradiation system comprising the beam monitor system according to claim 1.

7. A beam monitor system comprising a collection electrode for detecting a charged particle beam passing therethrough, a signal processing device, and a beam monitor controller, wherein:

the collection electrode includes a plurality of groups each of which is made up of a plurality of adjoining wire electrodes and divided into segments each including a plurality of adjoining wire electrodes, and each wire electrode in a segment in a group is connected to the signal processing device by using the same line as a wire electrode in a segment in each of the other groups, and the wire electrodes in each segment in each of the other groups are connected to the signal processing device by employing permutation connection varying from group to group so that no two adjoining channels are physically continuous, and the signal processing device, which is provided for performing signal processing on detection signals outputted from the wire electrodes of the collection electrode, rearranges the detection signals outputted from the wire electrodes in all ways corresponding to combinations of segments possible for all beam positions and outputs the result of each rearrangement as a processing signal, and the beam monitor controller performs calculation processing on each processing signal outputted from the signal processing device and determines deviation between a fitting function of beam distribution and the actual measurement value in regard to each channel, in terms of at least one selected from the absolute value of the difference between the fitting function and the actual measurement value, the sum of the absolute values of the differences, and the mean square of the differences, and the beam monitor controller judges that a case where the calculation result of the deviation is within a permissible value and is the minimum corresponds to the actual irradiation position and calculates the beam position and the beam width of the charged particle beam that passed through the wire electrodes based on the judgment.

8. A particle beam irradiation system comprising the beam monitor system according to claim 7.

* * * * *